United States Patent [19]

Ippen et al.

[11] Patent Number: 4,956,370
[45] Date of Patent: Sep. 11, 1990

[54] ANTIMYCOTICALLY ACTIVE SUBSTITUTED 2-AMINOTHIAZOLES

[75] Inventors: Joachim Ippen; Bernd Baasner; Albrecht Marhold, all of Leverkusen; Ernst Kysela, Bergisch-Gladbach; Klaus Schaller, Wuppertal; Miklos von Bittera, Leverkusen, all of Fed. Rep. of Germany

[73] Assignee: Bayer Aktiengesellschaft, Leverkusen, Fed. Rep. of Germany

[21] Appl. No.: 419,981

[22] Filed: Oct. 11, 1989

[30] Foreign Application Priority Data

Oct. 24, 1988 [DE] Fed. Rep. of Germany ....... 3836167
Nov. 25, 1988 [DE] Fed. Rep. of Germany ....... 3839758

[51] Int. Cl.$^5$ .................. C07D 417/12; A61K 31/505
[52] U.S. Cl. ..................................... 514/275; 544/331
[58] Field of Search ............... 548/193, 198; 544/331; 514/275

[56] References Cited

FOREIGN PATENT DOCUMENTS 3220118 12/1983 Fed. Rep. of Germany ...... 548/198

*Primary Examiner*—Robert Gerstl
*Attorney, Agent, or Firm*—Sprung Horn Kramer & Woods

[57] ABSTRACT

A 2-aminothiazole of the formula

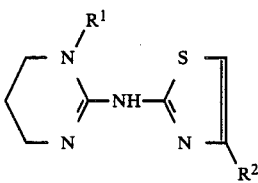

in which
 $R^1$ represents hydrogen or alkyl and
 $R^2$ represents a radical of the formula

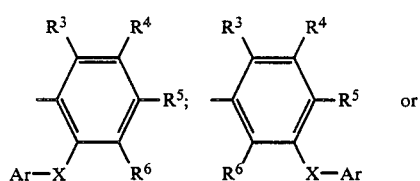 or

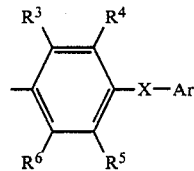

where
 $R^3$, $R^4$, $R^5$ and $R^6$ independently of one another in each case represent hydrogen, halogen, nitro, alkyl, alkoxy, alkoxycarbonyl, dialkylamino, alkylthio, alkylsulphinyl, alkylsulphonyl, halogenoalkyl, halogenoalkoxy, halogenoalkylthio, halogenoalkylsulphinyl or halogenoalkylsulphonyl,
 X represents oxygen, sulphur, sulphinyl or sulphonyl and
 Ar represents an unsubstituted aryl or a substituted aryl radical, and their physiologically tolerable acid addition salts.

6 Claims, No Drawings

ANTIMYCOTICALLY ACTIVE SUBSTITUTED 2-AMINOTHIAZOLES

The invention relates to new substituted 2-aminothiazoles, a process for their preparation and their use in combating diseases, in particular mycoses.

It is known that certain substituted aminothiazoles or their acid addition salts, such as, for example, the compound 4-(2,4-dichlorophenyl)-2-[2-(1,4,5,6-tetrahydropyrimidinyl)amino]thiazole hydrochloride or the compound 4-(4-chloro-3-methylphenyl)-2-[2-(1,4,5,6-tetrahydropyrimidinyl)amino]thiazole hydrochloride or the compound 4-(4-chloro-2-methoxyphenyl)-2-[2-(1,4,5,6-tetrahydropyrimidinyl)amino]thiazole possess good antimycotic properties (compare, for example, German Offenlegungsschrift No. 3,220,118).

The activity of these previously known compounds is not, however, completely satisfactory in all indications.

New 2-aminothiazoles of the general formula (I)

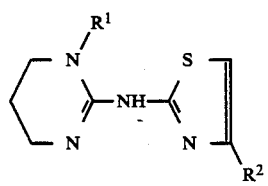

in which
R$^1$ represents hydrogen or alkyl and
R$^2$ represents a radical of the formula

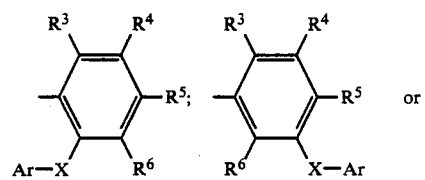

where
R$^3$, R$^4$, R$^5$ and R$^6$ independently case represent hydrogen, halogen, nitro, alkyl, alkoxy, alkoxycarbonyl, dialkylamino, alkylthio, alkylsulphinyl, alkylsulphonyl, halogenoalkyl, halogenoalkoxy, halogenoalkylthio, halogenoalkylsulphinyl or halogenoalkylsulphonyl,
X represents oxygen, sulphur, sulphinyl or sulphonyl and
Ar represents an optionally substituted aryl radical, and their physiologically tolerable acid addition salts have been found.

The compounds of the formula (I) are in equilibrium with the tautomeric compounds of the formulae (Ia) and (Ib)

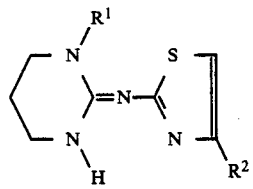

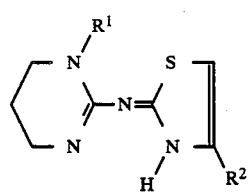

(where R$^1$ and R$^2$ in each case have the abovementioned meaning) which are also claimed according to the invention.

It has furthermore been found that the new substituted 2-aminothiazoles of the general formula (I)

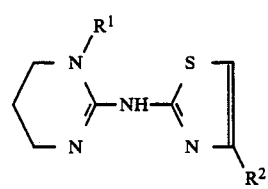

in which
R$^1$ represents hydrogen or alkyl and
R$^2$ represents a radical of the formula

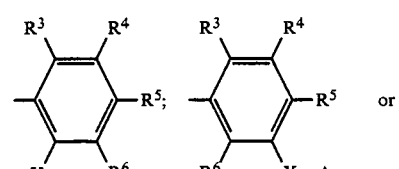

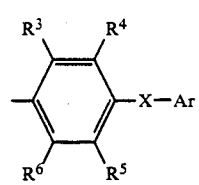

where
R$^3$, R$^4$, R$^5$ and R$^6$ independently of one another in each case represent hydrogen, halogen, nitro, alkyl, alkoxy, alkoxycarbonyl, dialkylamino, alkylthio, alkylsulphinyl, alkylsulphonyl, halogenoalkyl, halogenoalkoxy, halogenoalkylthio, halogenoalkylsulphinyl or halogenoalkylsulphonyl,
X represents oxygen, sulphur, sulphinyl or sulphonyl and
Ar represents an optionally substituted aryl radical, and their physiologically tolerable acid addition salts are obtained when thiourea derivatives of the formula (II)

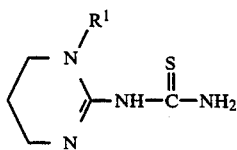
(II)

in which
R¹ has the abovementioned meaning, are reacted with acetophenone derivatives of the formula (III)

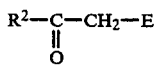
(III)

in which
R² has the abovementioned meaning and
E represents hydroxyl or halogen, if appropriate in the presence of a diluent and if appropriate in the presence of a reaction auxiliary and, if appropriate, an acid is then adducted.

Finally, it has been found that the new substituted 2-aminothiazoles of the general formula (I) possess good antimicrobial, in particular good antimycotic, properties.

Surprisingly, the substituted 2-aminothiazoles of the general formula (I) according to the invention show a considerably better antimycotic activity in certain indications than the substituted aminothiazoles and their acid addition salts known from the prior art, such as, for example, the compound 4-(2,4-dichlorophenyl)-2-[2-(1,4,5,6-tetrahydropyrimidinyl)amino]thiazole hydrochloride or the compound 4-(4-chloro-2-methylphenyl)-2-[2-(1,4,5,6-tetrahydropyrimidinyl)amino]thiazole hydrochloride or the compound 4-(4-chloro-2-methoxyphenyl)-2-[2-(1,4,5,6-tetrahydropyrimidinyl)amino]thiazole which, chemically and according to their action, are closely related compounds.

Formula (I) provides a general definition of the substituted 2-aminothiazoles according to the invention. Preferred compounds are those of the formula (I) in which
R¹ represents hydrogen or straight-chain or branched alkyl having 1 to 4 carbon atoms and
R² represents a radical of the formula

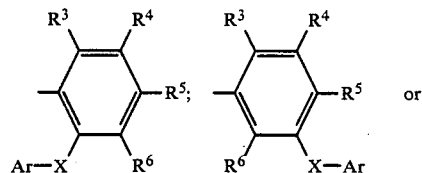

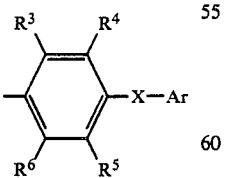

where
R³, R⁴, R⁵ and R⁶ independently of one another in each case represent hydrogen, fluorine, chlorine, bromine, iodine, nitro, in each case straight-chain or branched alkyl, alkoxy, alkoxycarbonyl, dialkylamino, alkylthio, alkylsulphinyl or alkylsulphonyl each having 1 to 4 carbon atoms in the respective alkyl moieties, or in each case straight-chain or branched halogenoalkyl, halogenoalkoxy, halogenoalkylthio, halogenoalkylsulphinyl or halogenoalkylsulphonyl each having 1 to 4 carbon atoms and 1 to 9 identical or different halogen atoms, in particular fluorine, chlorine, bromine or iodine,
X represents oxygen, sulphur, sulphinyl or sulphonyl and
Ar represents phenyl, α-naphthyl, β-naphthyl, tetrahydronaphthyl or indanyl which are in each case optionally monosubstituted or polysubstituted by identical or different substituents, suitable substituents in each case being: fluorine, chlorine, bromine, iodine, in each case straight-chain or branched alkyl, alkoxy, alkoxycarbonyl, dialkylamino, alkylthio, alkylsulphinyl or alkylsulphonyl each having 1 to 8 carbon atoms in the respective alkyl moieties, in each case straight-chain or branched halogenoalkyl, halogenoalkoxy, halogenoalkylthio, halogenoalkylsulphinyl or halogenoalkylsulphonyl each having 1 to 4 carbon atoms and to 9 identical or different halogen atoms, cycloalkyl having 3 to 7 carbon atoms, phenylalkyl or phenoxyalkyl each having 1 to 4 carbon atoms in the straight-chain or branched alkyl moiety and also phenyl or phenoxy.

Particularly preferred compounds are those of the formula (I) in which
R¹ represents hydrogen, methyl or ethyl,
R² represents a radical of the formula

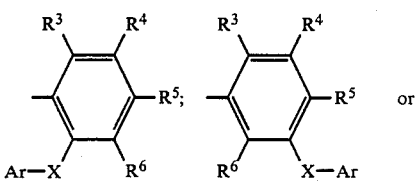

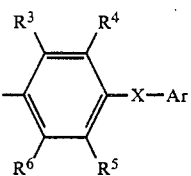

where
R³, R⁴, R⁵ and R⁶ independently of one another in each case represent hydrogen, fluorine, chlorine, bromine, nitro, methyl, ethyl, methoxy, ethoxy, methoxycarbonyl, ethoxycarbonyl, dimethylamino, diethylamino, methylthio, ethylthio, methylsulphinyl, ethylsulphinyl, methylsulphonyl or ethylsulphonyl, or halogenomethyl, halogenoethyl, halogenomethoxy, halogenoethoxy, halogenomethylthio, halogenoethylthio, halogenomethylsulphinyl, halogenoethylsulphinyl, halogenomethylsulphonyl or halogenoethylsulphonyl each having 1 to 5 identical or different halogen atoms, in particular fluorine, chlorine or bromine,
X represents oxygen, sulphur, sulphinyl or sulphonyl and Ar represents phenyl, α-naphthyl, β-naphthyl, tetrahydronaphthyl or indanyl which are in each case optionally monosubstituted to pentasubstituted by identical or different substituents, suitable substituents in each case being: fluorine, chlorine, bromine, nitro, in each case straight-chain or branched alkyl, alkoxyl, alkoxycarbonyl or dialkylamino each having 1 to 6 carbon atoms in the respective alkyl moieties, in each case straight-chain or branched alkylthio, alkylsulphinyl or alkylsulphonyl each having 1 to 3 carbon atoms, in each case straight-chain or branched halogenoalkyl, halogenoalkoxy, halogenoalkylthio, halogenoalkylsulphinyl or halogenoalkylsulphonyl each having 1 to 3 carbon atoms and 1 to 7 identical or different halogen atoms, in particular fluorine, chlorine or bromine, cyclohexyl having 3 to 6 carbon atoms, phenylalkyl or phenoxyalkyl each having 1 to 3 carbon atoms in the straight-chain or branched alkyl moiety and also phenyl or phenoxy.

Very particularly preferred compounds are those of the formula I in which $R^1$ represents hydrogen or methyl and
$R^2$ represents a radical

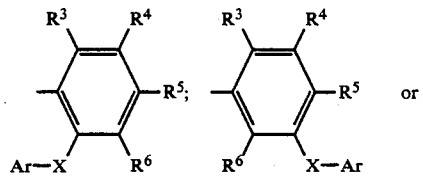 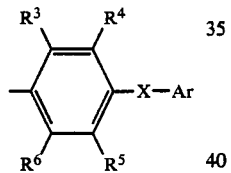 or

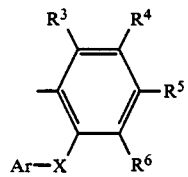

where $R^3$, $R^4$, $R^5$ and $R^6$ independently of one another in each case represent hydrogen, fluorine, chlorine, nitro, methyl, methoxy, ethoxycarbonyl, methoxycarbonyl, dimethylamino, methylthio, trifluoromethyl, trifluoromethoxy, trifluoromethylthio, trifluoromethylsulphinyl or trifluoromethylsulphonyl, X represents oxygen or sulphur and Ar represents phenyl, α-naphthyl, β-naphthyl, tetrahydronaphthyl or indanyl which are in each case optionally monosubstituted to tetrasubstituted by identical or different substituents, suitable substituents in each case being: fluorine, chlorine, bromine, nitro, methyl, ethyl, n- or i-propyl, n-, i-, s- or t-butyl, methoxy, ethoxy, n- or i-propoxy, methoxycarbonyl, ethoxycarbonyl, dimethylamino, diethylamino, methylthio, ethylthio, methylsulphinyl, methylsulphonyl, trifluoromethyl, trifluoromethoxy, trifluoromethylthio, trifluoromethylsulphinyl, trifluoromethylsulphonyl, cyclopentyl, cyclohexyl, benzyl, phenylethyl, phenylpropyl, phenoxymethyl, phenyl or phenoxy.

Very particularly preferred compounds according to the invention are also addition products of acids and those substituted 2-aminothiazoles of the formula (I) in which the substituents $R^1$ and $R^2$ have the meanings which have already been mentioned as preferred for these substituents.

The acids which can be adducted preferably include hydrohalic acids, such as, for example, hydrochloric acid and hydrobromic acid, in particular hydrochloric acid, and in addition phosphoric acid, nitric acid, sulphuric acid, mono-, bi- and trifunctional carboxylic acids and hydroxycarboxylic acids, such as, for example, acetic acid, oxalic acid, maleic acid, malonic acid, succinic acid, fumaric acid, glutaric acid, hydroxyglutaric acid, adipic acid, oleic acid, tartaric acid, malic acid, citric acid, benzoic acid, salicylic acid, sorbic acid and lactic acid, sulphonic acids, such as, for example, methanesulphonic acid, p-chlorobenzenesulphonic acid, p-toluenesulphonic acid and 1,5-naphthalenedisulphonic acid, sulphuric acid half esters such as sulphuric acid monomethyl ester or sulphuric acid monoethyl ester and also saccharin or thiosaccharin.

Particularly preferred compounds of the formula (I) are those in which $R^1$ represents hydrogen and
$R^2$ represents a radical of the formula

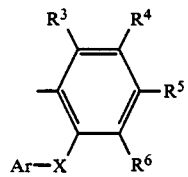

where $R^3$, $R^4$, $R^5$ and $R^6$ independently of one another in each case represent hydrogen, fluorine, chlorine, methyl or nitro, X represents oxygen and Ar represents phenyl which is optionally monosubstituted to trisubstituted by identical or different substituents, suitable substituents in particular being: fluorine, chlorine, nitro, methyl, ethyl, n- or i-propyl, n-, i-, s- or t-butyl, methoxy, methylthio, trifluoromethyl, trifluoromethoxy, trifluoromethylthio, trifluoromethylsulphinyl, trifluoromethylsulphonyl, cyclopentyl, cyclohexyl, phenyl or phenoxy.

Particularly preferred compounds of the formula (I) are in addition also those in which $R^1$ represents hydrogen and
$R^2$ represents a radical of the formula

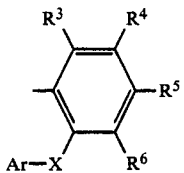

where $R^3$, $R^4$, $R^5$ and $R^6$ independently of one another in each case represent hydrogen, fluorine, chlorine, methyl or nitro, X represents oxygen and Ar represents phenyl which is at least monosubstituted by trifluoromethylthio, it being possible for one to three identical or different additional substituents to be present and suitable additional substituents being: fluorine, chlorine, methyl, ethyl, n- or i-propyl, n-, i-, s- or t-butyl, methoxy, trifluoromethyl, trifluoromethoxy and trifluoromethylthio.

If, for example, N-(1,4,5,6-tetrahydro-2-pyrimidinyl)-thiourea and 2-bromoacetyl-4'-trifluoromethylthio diphenyl ether are used as starting substances, the course of the reaction of the process according to the invention can be represented by the following equation:

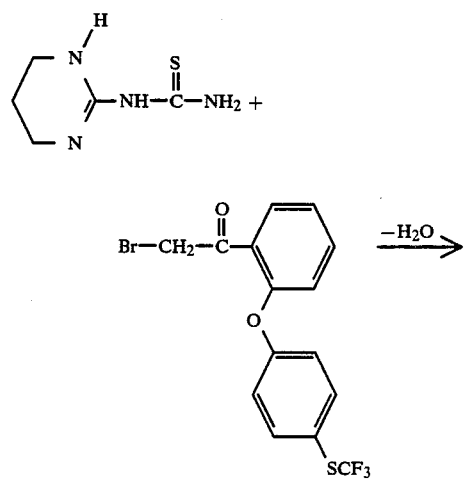

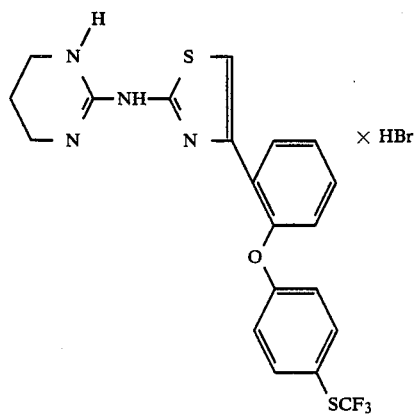

Formula (II) provides a general definition of the thiourea derivatives required as starting substances for carrying out the process according to the invention. In this formula (II), $R^1$ preferably represents those radicals which have already been mentioned as preferred for this substituent in connection with the description of the substances of the formula (I) according to the invention.

The thiourea derivatives of the formula (II) are known (compare, for example, Arzneim.-Forsch. 35, 573–577 [1985] or German Offenlegungsschrift No. 3,220,118 or EP No. 95,640) or can be obtained in analogy to known processes (compare, for example, Organic Syntheses, Coll. Vol. IV, 502), for example when tetrahydropyrimidinylcyanamides of the formula (XI)

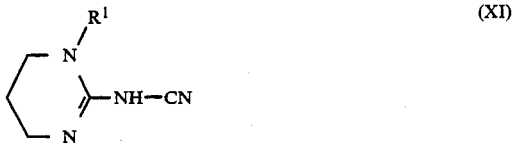

in which $R^1$ has the abovementioned meaning, are reacted with hydrogen sulphide, if appropriate in the presence of a diluent such as, for example, water and if appropriate in the presence of a reaction auxiliary such as, for example, sodium hydroxide, at temperatures between 20° C. and 120° C.

Tetrahydropyrimidinylcyanamides of the formula (XI) are known (compare, for example, German Offenlegungsschrift No. 2,205,745; German Offenlegungsschrift No. 2,205,744; J. Org. Chem. 38, 155–156 [1973]).

Formula (III) provides a general definition of the acetophenone derivatives furthermore required as starting substances for carrying out the process according to the invention. In this formula (III), $R^2$ preferably represents those radicals which have already been mentioned as preferred for this substituent in connection with the description of the substances of the formula (I) according to the invention.

E preferably represents hydroxyl, chlorine or bromine.

Acetophenone derivatives of the formula (III) are known in some cases (compare, for example, Chem. Pharm. Bull. 32, 3066–3074 [1984]; German Offenlegungsschrift No. 3,529,646; JP No. 62/19,566; J. Chem. Soc. Perkin I, 1983, 1483–1488; J. Med. Chem. 26, 1353–1360 [1983]; J. Chem. Soc. Perkin I, 1978, 446–451; Isr. J. Chem. 1974, 12, 977–979).

The invention also relates to hitherto unknown acetophenone derivatives of the formula (IIIa)

in which $Hal^1$ represents chlorine or bromine and
$R^{2-1}$ represents a radical of the formula

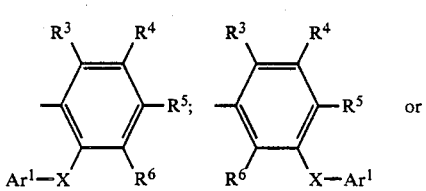

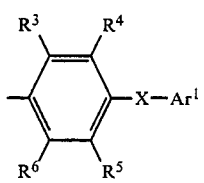

where $R^3$, $R^4$, $R^5$, $R^6$ and X in each case have the abovementioned meaning and $Ar^1$ represents an optionally substituted aryl radical, where at least one substituent represents fluorine, halogenoalkyl, halogenoalkoxy, halogenoalkylthio, halogenoalkylsulphinyl or halogenoalkylsulphonyl and where the meaning 2-chloro-4-trifluoromethylphenyl is excluded for $Ar^1$.

Known and unknown acetophenone derivatives of the formula (III) are obtained in analogy to known processes, for example when acetophenones of the formula (IV)

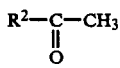  (IV)

in which
  $R^2$ has the abovementioned meaning, are reacted with halogenating agents such as, for example, sulphuryl chloride or bromine, if appropriate in the presence of a diluent such as, for example, dichloromethane or glacial acetic acid and if appropriate in the presence of a reaction auxiliary such as, for example, hydrochloric acid, at temperatures between −20° C. and +80° C., or when diaryl (thio)ether derivatives of the formula (V)

$R^2$—H  (V)

in which
  $R^2$ has the abovementioned meaning, are reacted with chloroacetyl chloride or bromoacetyl bromide, if appropriate in the presence of a diluent such as, for example, dichloromethane and if appropriate in the presence of a reaction auxiliary such as, for example, aluminium trichloride, at temperatures between −20° C. and +120° C. (compare, for example, J. Org. Chemistry 40, 2304–2307 [1975]).

Acetophenones of the formula (IV) are known in some cases (compare, for example, Chem. Pharm. Bull. 23, 2223–2231 [1975]; Collect. Czech. Chem. Commun. 51, 2598–2616 [1986]; J. Org. Chem. 43, 1763–1768 [1978]; JP No. 56/2925; Chem. Ber. 120, 1151–1173 [1987]; Anal. Chim. Acta 54, 321–336 [1971]).

The invention also relates to hitherto unknown acetophenones of the formula (IVa)

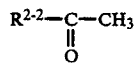  (IVa)

in which
  $R^{2-2}$ represents a radical of the formula

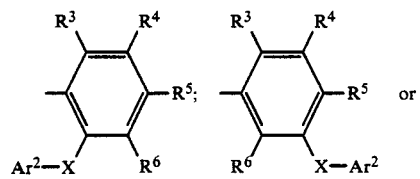

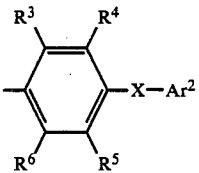

where
  $R^3$, $R^4$, $R^5$, $R^6$ and X in each case have the above mentioned meaning and
  $Ar^2$ represents an optionally substituted aryl radical, where at least one substituent represents halogenoalkoxy, halogenoalkylthio, halogenoalkylsulphinyl or halogenoalkylsulphonyl.

Known and unknown acetophenones of the formula (IV) are obtained in analogy to known processes, for example when halogenoacetophenones of the formula (VI)

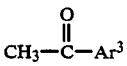  (VI)

in which
  $Ar^3$ represents a radical of the formula

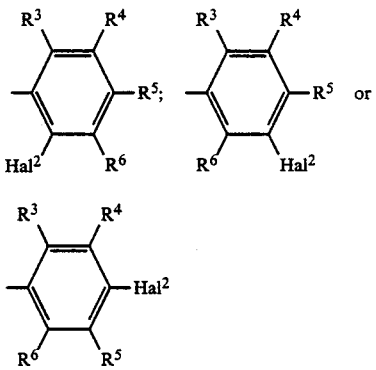

where
  $Hal^2$ in each case represents chlorine or bromine and
  $R^3$, $R^4$, $R^5$ and $R^6$ in each case have the abovementioned meaning,
are reacted with phenols of the formula (VII)

Ar—OH  (VII)

in which
  Ar has the abovementioned meaning,
  if appropriate in the presence of a diluent such as, for example, dioxane, if appropriate in the presence of a reaction auxiliary such as, for example, potassium hydroxide and if appropriate in the presence of a catalyst such as, for example, copper or palladium, at temperatures between 50° C. and 150° C., or when diaryl(thio)ether derivatives of the formula (V)

$R^2$—H  (V)

in which
  $R^2$ has the abovementioned meaning, are reacted with acetylating agents such as, for example, acetyl chloride or acetic anhydride, if appropriate in the presence of a diluent such as, for example, dichloromethane and if appropriate in the presence of a reaction auxiliary such as, for example, aluminium trichloride, at temperatures between −20° C. and +120° C. (compare, for example, J. Org. Chem. 40, 2304–2307 [1975]), or when aniline derivatives of the formula (VIII)

  (VIII)

R²—NH₂ in which

R² has the abovementioned meaning, are first diazotized with sodium nitrite in the presence of an acid such as, for example, hydrochloric acid in a customary manner, at temperatures between −20° C. and +20° C. and subsequently reacted with acetaldoxime in the presence of a reaction auxiliary such as, for example, sodium acetate and also if appropriate in the presence of a catalyst such as, for example, copper(II) sulphate, at temperatures between 0° and 30° C. and subsequently the acetophenone oximes thus obtainable of the formula (IX)

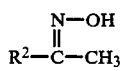  (IX)

in which

R² has the abovementioned meaning, are hydrolyzed with concentrated hydrochloric acid at temperatures between 80° C. and 150° C. (compare, for example, J. Chem. Soc. 1954, 1297; J. Med. Chem. 26, 1353 [1983]), or when benzonitrile derivatives of the formula (X)

  (X)

R²—CN in which

R² has the abovementioned meaning, are reacted with methylmagnesium bromide in the presence of a diluent such as, for example, diethyl ether and if appropriate in the presence of a catalyst such as, for example, copper(I) chloride, at temperatures between −20° C. and +50° C. and subsequently the acetophenones obtainable with the aid of the processes described above of the formula (IVb)

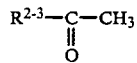  (IVb)

in which

R²⁻³ represents a radical of the formula

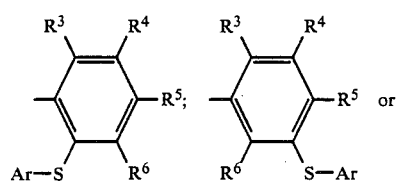

-continued

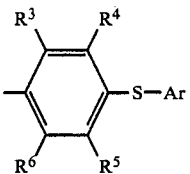

where

R³, R⁴, R⁵, R⁶ and Ar in each case nave the abovementioned meaning, are optionally oxidized at the sulphur with customary oxidizing agents such as, for example, 3-chloroperbenzoic acid, if appropriate in the presence of a diluent such as, for example, dichloromethane, at temperatures between 0° C. and 50° C. (compare also the preparation examples).

Diaryl thioether derivatives of the formula (V) are known or obtainable in analogy to known processes (compare, for example, Synth. Commun. 17, 685–692 [1987]).

Halogenoacetophenones of the formula (VI) are known or obtainable in analogy to known processes (compare, for example, J. Org. Chem. 46, 2169–2171 [1981]; J. Chem. Soc. Perkin Trans. I, 1974, 1769–1771).

Phenols of the formula (VII) are, for the most part, generally known compounds of organic chemistry compare, for example, DE No. 1,257,784). Some of them are also the subject of a parallel patent application by the parent company.

The present invention therefore also relates to new fluorine-containing phenols of the formula (VIIa)

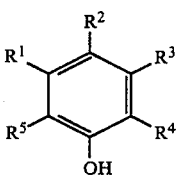  (VIIa)

in which one of the radicals R¹ and R² represents OCF₃, OCF₂CFClH,
OCF₂CF₂H, SCF₂CF₂H or SCF₂CFClH and the other of the radicals R¹ and R² represents hydrogen or C₁- to C₄-alkyl, R³ represents hydrogen, chlorine or OCF₃, R⁴ represents hydrogen, C₁- to C₄-alkyl, NO₂, chlorine, CONH₂ or COOH and R₅ represents hydrogen, chlorine or NO₂, where one of the radicals R¹ and R² may also represent SCF₃ if R⁴ represents NO₂, CONH₂ or COOH.

If the substituents mentioned are C₁- to C₄-alkyl, methyl and ethyl are preferred, in particular methyl.

Preferred compounds of the formula (VIIa) are those in which

R¹ represents hydrogen,

R² represents OCF3₃ or OCF₂CFClH,

R³ represents hydrogen or chlorine,

R⁴ represents methyl, NO₂, chlorine or CONH₂ and

R⁵ represents hydrogen, chlorine or NO₂.

Examples of preferred compounds of this type are those in which (radicals not mentioned=hydrogen):

R²=OCF₃, R⁴=methyl,

R²=OCF₂CFClH, R⁴=methyl,

R²=OCF₃, R⁴=NO₂, $R^2$=OCF$_3$, $R^3$=$R^4$=$R^5$=chlorine,
$R^2$=OCF$_3$, $R^4$=CONH$_2$ and
$R^2$=OCF$_3$, $R^4$=$R^5$=NO$_2$.

Particularly preferred compounds of the formula (VIIa) are those in which
$R^1$ represents hydrogen,
$R^2$ represents OCF$_3$ or OCF$_2$CFClH,
$R^3$ represents hydrogen or chlorine,
$R^4$ represents methyl, NO$_2$ or chlorine and
$R^5$ represents hydrogen or chlorine.

Example of particularly preferred compounds of this type are those in which (radicals not mentioned=hydrogen):
$R^2$=OCF$_3$, $R^4$=methyl,
$R^2$=OCF$_2$CFClH, $R^4$=methyl,
$R^2$=OCF$_3$, $R^4$=NO$_2$ and
$R^2$=OCF$_3$, $R^3$=$R^4$=$R^5$=chlorine.

A very particularly preferred compound of the formula (VIIa) is 2-methyl-4-trifluoromethoxybenzene.

The fluorine-containing phenols according to the invention may be prepared in various ways.

For example, according to a first method substituents can be introduced into the 2-position and, if desired, additionally into the 3- and/or 6-position in a phenol of the formula (VIIb)

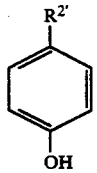

(VIIb)

in which
$R^{2'}$ represents OCF$_3$, OCF$_2$CFClH, OCF$_2$CF$_2$H, SCF$_2$CFClH or SCF$_2$CF$_2$H.

When introducing an NO$_2$, COOH or CONH$_2$ group, $R^2$ may also represent SCF$_3$ in the starting phenol of the formula (VIIb).

For example, chlorine atoms can thus be introduced by reaction with a chlorinating agent. A suitable chlorinating agent is, for example, elemental chlorine. Suitable temperatures in this case are those from, for example, 0° to 50° C. The reaction is expediently carried out in the presence of a catalyst, for example iron, and an inert solvent, for example a chlorinated hydrocarbon.

Nitro groups can be introduced, for example, by reaction with nitric acid. Depending on the reaction temperature and concentration of the nitric acid, for example, one (in the 2-position) or two nitro groups (in the 2- and 6-position) can be introduced. An NO$_2$ group can be introduced, for example, using 20 to 33% strength by weight nitric acid at 10° to 30° C., two NO$_2$ groups, for example, using 37 to 60% strength by weight HNO$_3$ at 50° to 80° C.

Carboxyl groups can be introduced, for example, by reacting with carbon dioxide under elevated pressure, at elevated temperature and in the presence of a base. A suitable base is, for example, potassium carbonate, suitable pressures, are, for example, those from 10 to 100 bar, suitable temperatures are, for example, those from 150° to 250° C.

Acid amide groups can be introduced, for example, by first reacting carboxyl groups, optionally introduced as described above, with SOCl$_2$ in the presence of a solvent and then with ammonia.

For example, according to a second method an aniline of the formula (VIIIa)

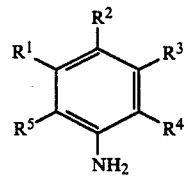

(VIIIa)

in which the radicals $R_1$ to $R_5$ have the meaning indicated in formula (VIIa) can be diazotized and boiled. The diazotization can be carried out, for example, using sodium nitrite in the presence of hydrochloric acid, the boiling, for example, with azeotropic removal of water in the presence of sulphuric acid at temperatures around 100° to 130° C.

For example, according to a third method a compound of the formula (VIIc)

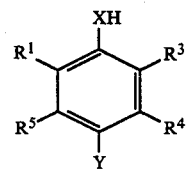

(VIIc)

in which
X represents oxygen or sulphur,
Y represents OH, NHacetyl or NO$_2$ and
$R^3$ represents hydrogen or C$_1$- to C$_4$-alkyl and
$R^1$ to $R^5$ have the meaning indicated in formula (VIIa) can be reacted with tetrafluoroethylene and, in the case where Y=NHacetyl or NO$_2$, these groups can be converted into an OH group in a manner known per se. If X represents oxygen, Y preferably represents NHacetyl or NO$_2$, if X represents sulphur, Y preferably represents OH.

This method is particularly suitable for the preparation of fluorine-containing phenols of the formula (VIIa) in which $R^2$ represents OCF$_2$CF$_2$H or SCF$_2$CF$_2$H. Reaction with tetrafluoroethylene is preferably carried out in this case in the presence of a base and a dipolar, aprotic solvent, for example at temperatures in the range 50° to 150° C.

It is decidedly surprising that the compounds of the formula (VIIa) according to the invention are accessible in such good yields and selectivities, since, to a large extent, the occurrence of undesired side reactions had to be taken into account in the many conceivable possibilities for substitution, elimination and addition of the educts to be employed and the products obtained. In spite of this, the compounds of the formula (VIIa) according to the invention can frequently be obtained in yields of over 70% of theory.

The present invention also relates to 4-trifluoromethylmercaptophenols of the formula (VIId)

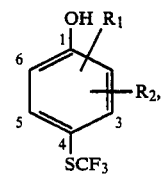

(VIId)

in which $R_1$ and $R_2$ independently of one another in each case represent $C_1$- to $C_4$-alkyl, optionally substituted $C_1$- to $C_4$-alkoxy, optionally substituted $C_1$- to $C_4$-alkylthio and/or halogen or $R_1$ represents hydrogen and $R_2$ represents $C_2$- to $C_4$-alkyl, optionally substituted $C_1$- to $C_4$-alkoxy, optionally substituted $C_1$- to $C_4$-alkylthio or fluorine.

Suitable substituents in optionally substituted $C_1$- to $C_4$-alkoxy and in optionally substituted $C_1$- to $C_4$-alkylthio are preferably halogens, in particular fluorine.

If $R_1$ and $R_2$ denote halogen, fluorine, chlorine, bromine and/or iodine are suitable.

Preferably, $R_1$ and $R_2$ independently of one another in each case represent methyl, ethyl, isopropyl, methoxy, fluoromethoxy, fluoroethoxy, fluoropropoxy, fluorobutoxy, fluoromethylthio, fluoroethylthio, fluoropropylthio, fluorobutylthio, fluorine, chlorine or bromine or $R_1$ represents hydrogen and $R_2$ represents ethyl, isopropyl, methoxy, fluoromethoxy, fluoroethoxy, fluoropropoxy, fluorobutoxy, fluoromethylthio, fluoroethylthio, fluoropropylthio, fluorobutylthio, fluorine, chlorine or bromine, $C_1$- to $C_4$-alkyl preferably represents methyl, ethyl or isopropyl, $C_2$- to $C_4$-alkyl preferably represents ethyl or isopropyl. Optionally substituted $C_1$- to $C_4$-alkoxy preferably represents methoxy, difluoromethoxy, difluorochloromethoxy, trifluoromethoxy, trifluoroethoxy, tetrafluoroethoxy, trifluorochloroethoxy, hexafluoropropoxy or hexafluorobutoxy.

Optionally substituted $C_1$- to $C_4$-alkylthio preferably represents difluoromethylthio, difluorochloromethylthio, trifluoromethylthio, trifluoroethylthio, tetrafluoroethylthio, trifluorochloroethylthio, hexafluoropropylthio or hexafluorobutylthio.

Halogen preferably represents fluorine, chlorine or bromine.

$R_1$ and $R_2$ may assume any position in the aromatic ring, i.e. with $R_1$ in the 2-position, $R_2$ may be present in the 3-, 5- or 6-position and with $R_1$ in the 3-position, $R_2$ may be present in the 2-, 5- and 6-position. The possible isomers in which R is in the 4- or 5-position are identical with the abovementioned.

Particularly preferred individual compounds embraced by the formula (VIId) contain the following radicals $R_1$ and $R_2$ in the positions indicated in each case:

$R_1$=3-H, $R_2$=1-ethyl; $R_1$=3-H, $R_2$=2-isopropyl; $R_1$=3H, $R_2$=2-methoxy; $R_1$=$R_2$=2,6-dimethyl; $R_1$=$R_2$=2,3-dimethyl; $R_1$=$R_2$=3,5-dimethyl; $R_1$=$R_2$=2,5-dimethyl; $R_1$=2-methyl, $R_2$=5-chlorine; $R_1$2-methyl, $R_2$3-chlorine; $R_1$=2-ethyl, $R_2$=3-methyl; $R_1$=2-ethyl, $R_2$=3-fluorine; $R_1$=2-methyl, $R_2$=3-fluorine; $R_1$=2-methyl, $R_2$=6-fluorine; $R_2$=2-methyl, $R_2$=5-fluorine; $R_1$=3-methyl, $R_2$=6-chlorine and $R_2$=2-methyl, $R_2$=6-chlorine.

The present invention also relates to a process for the preparation of compounds of the formula (VIId), which is characterized in that a phenol of the formula (VIIe)

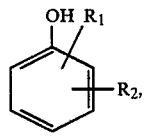
(VIIe)

in which $R_1$ and $R_2$ have the meaning indicated in formula (VIId), is reacted with trifluoromethylsulphenyl chloride.

The reaction according to the invention for the preparation of compounds of the formula (VIId) can be carried out at atmospheric pressure, elevated pressure or reduced pressure. Preferably, the reaction is carried out at atmospheric pressure.

The reaction according to the invention for the preparation of compounds of the formula (VIId) can be carried out, for example, at temperatures in the range −20° to +100° C. Preferably, the reaction is carried out at temperatures in the range from 0° to 60° C.

The reaction components can in principle be employed in any proportions. Preferably, 1 to 10 moles of the respective phenol of the formula (VIIe) are employed per mole of trifluoromethylsulphenyl chloride. Particularly preferably, 1.05 to 8 moles of the respective phenol of the formula (VIIe) are employed per mole of trifluoromethylsulphenyl chloride. When using phenol in excess, quantitative consumption of the trifluoromethylsulphenyl chloride and formation of fewer by-products can generally be achieved.

The reaction according to the invention for the preparation of compounds of the formula (VIId) can be carried out in the presence or absence of catalysts. Preferably, the reaction is carried out in the presence of catalysts, since then it can advantageously generally also be carried out at relatively low temperatures. Suitable catalysts are, for example, Lewis acids or bases. Examples of Lewis acids are iron trichloride, titanium tetrachloride, boron trifluoride, antimony pentachloride and aluminum trichloride. Lewis acids can be employed, for example, in amounts from 0.01 to 0.2 moles per mole of trifluoromethylsulphenyl chloride. Examples of bases are alkali metal carbonates, triphenylphosphine and tertiary nitrogen bases. Tertiary amines such as pyridine, picoline, triethylamine, 1,5-diazabicyclobicyclo[4.3.0]-non-5-ene and 1,8-diazabicyclo[5.4.-0]undec-7-ene are preferred. Bases can, for example, be employed in the same or a higher molar amount than trifluoromethylsulphenyl chloride.

The reaction according to the invention for the preparation of compounds of the formula (VIId) can be carried out in the presence or absence of solvents. Suitable solvents are, for example, ethers or halogenoalkanes.

Phenols of the formula (VIIe) are known and easily accessible. Trifluoromethylsulphenyl chloride is also known and easily accessible.

After carrying out the reaction according to the invention for the preparation of compounds of the formula (VIId), reaction mixtures are frequently obtained which, in addition to the desired product, also contain bistrifluoromethylmercaptophenols and possibly unreacted starting phenol and therefore have to be worked up. The separation of the reaction mixture is in most cases possible by distillation through a column, particularly when little or no bis-trifluoromethylmercaptophenols are present. In some cases one component also crystallizes out from the reaction mixture, for example excess starting phenol or the 4-trifluoromethylmercaptophenol formed, and can then be separated off by filtration.

A particular form of working up the reaction mixture consists in first separating off any solvents, catalysts and/or hydrochlorides of bases which may be present, for example by filtration and/or simple distillation, and then separating these by column chromatography on silica gel. A hydrocarbon, in particular toluene, can, for example, be used as the mobile phase. In general, the bis-trifluoromethylmercapto-substituted phenol is then obtained as the first fraction and the 4-trifluoromethylmercaptophenol of the formula (VIId) as the second fraction. The latter can be obtained in pure form by removing the mobile phase employed for the separation by column chromatography, for example toluene, from the corresponding fraction, for example by distillation.

The present invention furthermore relates to 4-trifluoromethylsulphonylphenols of the formula (VIIf)

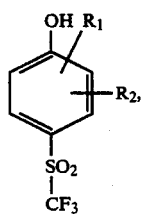

(VIIf)

in which $R_1$ and $R_2$ have the meaning indicated in formula (VIId). The preferred and particularly preferred meanings of $R_1$ and $R_2$ in formula (VIIf) are also as indicated in formula (VIId).

Finally, the present invention also relates to a process for the preparation of 4-fluoromethylsulphonylphenols of the formula (VIIf). This process is characterized in that a 4-trifluoromethylmercaptophenol of the formula (VIId) is oxidized at elevated temperature in the presence of an acid using an activated oxidizing agent containing oxygen.

Temperatures in the range 50° to 120° C., for example, are suitable for this oxidation. Preferably, the oxidation is carried out at 65° to 100° C.

Suitable acids are, for example, organic acids, such as aliphatic carboxylic acids having 1 to 6 C atoms and optionally substituted by halogen, but also mineral acids such as phosphoric acid or sulphuric acid. Acetic acid, propionic acid, chloroacetic acid and trifluoroacetic acid are preferred. Acetic acid is particularly preferred.

Suitable activated oxidizing agents containing acids, Caro's acid and its salts, peroxodisulphate and molecular oxygen in combination with catalysts. Hydrogen peroxide, Caro's acid and its salts, in particular hydrogen peroxide, which can be employed, for example, in 10 to 50% strength by weight aqueous solution are preferably employed. The oxidizing agent employed in each case may optionally be dissolved in water and/or an organic solvent. The oxidizing agents containing active oxygen which are employed do not necessarily have to react with the compound of the formula (VIId) in the form employed, but they can also be converted completely or partially into other oxidizing agents containing activated oxygen before this reaction. For example, Caro's acid can be formed from hydrogen peroxide and sulphuric acid or peracetic acid from hydrogen peroxide and acetic acid. Similarly, the oxidizing agents containing activated oxygen which are in each case desired, can also first be allowed to form in situ, for example Caro's acid from hydrogen peroxide and sulphuric acid.

The oxidizing agent is preferably employed in the stoichiometrically required amount or in an excess of up to 100 mol %.

The process according to the invention for the preparation of 4-trifluoromethylsulphonylphenols of the formula (VIIf) can be carried out in the presence or absence of solvents. Suitable solvents are, for example, ethers, such as dioxane or diglyme. When working in the presence of organic acids, in particular acetic acid, the acid may also function as the solvent.

The working up of the reaction mixture may be carried out, for example, so that any excess oxidizing agent present is destroyed and the 4-trifluoromethylsulphonylphenol of the formula (VIIf) is then precipitated by pouring into water or made to crystallize by distilling off solvent and/or acid and then in each case filtered.

It is decidedly surprising that 4-trifluoromethylsulphonylphenols can be obtained from the corresponding mercaptophenols in good yields according to the invention, since a large number of processes are known in which the corresponding quinones are formed from phenols by oxidation using hydrogen peroxide or peracids.

Aniline derivatives of the formula (VII) are known or are obtainable in analogy to known processes (compare, for example, EP No. 34,771; J. Chem. Soc. Perkin Trans I, 1976, 1279–1285).

Benzonitrile derivatives of the formula (X) are known or are obtainable in analogy to known processes (compare, for example, U.S. Pat. No. 3,950,379; J. Med. Chem. 29, 427–433 [1986]).

Suitable diluents for carrying out the process according to the invention are inert organic or inorganic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoramide, esters, such as ethyl acetate or sulphoxides, such as dimethyl sulphoxide, alcohols such as methanol, ethanol or propanol, bases such as pyridine and, if appropriate, also their mixtures with water or pure water.

The process according to the invention is optionally carried out in the presence of a suitable reaction auxiliary. Those suitable are all customary inorganic or organic bases. These include, for example, alkali metal hydroxides, such as sodium hydroxide or potassium hydroxide, alkali metal carbonates, such as sodium carbonate, potassium carbonate or sodium hydrogencarbonate, ammonia and primary, secondary or tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperatures can be varied within a relatively wide range when carrying out the process according to the invention. In general, the process is carried out at temperatures between 0° C. and 180° C., preferably at temperatures between 20° C. and 150° C.

In order to carry out the process according to the invention, 1.0 to 1.5 moles, preferably 1.0 to 1.2 moles of ketone derivative of the formula (III) and, if appropriate, 1.0 to 1.2 moles, preferably 1.0 to 1.2 moles, of reaction auxiliary are generally employed per mole of thiourea derivative of the formula (II). The reaction is carried out and worked up and the reaction products are isolated by generally customary methods. Any by-products which occur can be separated off using customary chromatographic methods.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and can be isolated in a known manner, for example by filtration, and, if appropriate, purified by washing with an inert organic solvent.

The compounds of the formula (I) according to the invention and their acid addition salts exhibit antimicrobial, in particular strong antibacterial and antimycotic, actions. They possess a very wide antimycotic spectrum of action, in particular against dermatophytes and Blastomyces and also biphasic fungi, for example against Candida species, such as *Candida albicans,* Epidermophyton species, such as *Epidermophyton floccosum,* Aspergillus species, such as *Aspergillus niger* and *Aspergillus fumigatus,* Trichophyton species, such as *Trichophyton mentagrophytes,* Microsporon species, such as *Microsporon felineum* and and Torulopsis species, such as *Torulopsis glabrata.* The enumeration of these microorganisms in no way represents a limitation of the microorganisms which can be combated, but is only of illustrative character.

Examples of indications in human medicine which may be mentioned, for example, are: dermatomycoses and systemic mycoses produced by *Trichophyton mentagrophytes* and other Trichophyton species, Microsporon species and also *Epidermophyton fluccosum,* Blastomycetes and biphasic fungi and also Hyphomycetes.

Indication areas which may be mentioned in veterinary medicine are: all dermatomycoses and systemic mycoses, in particular those which are produced by the abovementioned pathogens.

The present invention includes pharmaceutical preparations which contain one or more active compounds according to the invention or which consist of one or more active compounds according to the invention in addition to non-toxic, inert pharmaceutically suitable excipients.

The present invention also includes pharmaceutical preparations in dosage units. This means that the preparations are present in the form of individual parts, for example tablets, coated tablets, capsules, pills, suppositories and ampoules, whose content of active compound corresponds to a fraction or a multiple of an individual dose. The dosage units may contain, for example, 1, 2, 3 or 4 individual doses or $\kappa$, $\frac{1}{3}$ or $\frac{1}{4}$ of an individual dose. An individual dose preferably contains the amount of active compound which is administered in one administration and which usually corresponds to a whole, a half, a third or a quarter of a daily dose.

Non-toxic, inert pharmaceutically suitable excipients are taken to mean solid, semisolid of liquid diluents, fillers or formulation auxiliaries of any type.

Preferred pharmaceutical preparations which may be mentioned are tablets, coated tablets, capsules, pills, granules, suppositories, solutions, suspensions and emulsions, pastes, ointments, gels, creams, lotions, powders or sprays.

Tablets, coated tablets, capsules, pills and granules may contain the active compound or compounds in addition to the customary excipients, such as (a) fillers and extenders, for example starches, lactose, sucrose, glucose, mannitol and silica, (b) binders, for example carboxymethylcellulose, alginates, gelatin, polyvinylpyrrolidone, (c) humectants, for example glycerol, (d) disintegrants, for example agar-agar, calcium carbonate and sodium bicarbonate, (e) solution retardants, for example paraffin and (f) absorption accelerators, for example quaternary ammonium compounds, (g) wetting agents, for example cetyl alcohol, glycerol monostearate, (h) adsorption agents, for example kaolin and bentonite and (i) lubricants, for example talc, calcium stearate and magnesium stearate and solid polyethylene glycols or mixtures of the substances mentioned under (a) to (i).

The tablets, coated tablets, capsules, pills and granules can be provided with the customary coatings and coverings, optionally containing an opacifying agent, and can be composed so that they release the active compound or compounds only or preferably in a certain part of the intestinal tract, if desired in a sustained manner, it being possible to use, for example, polymer substances and waxes as embedding materials.

The active compound or compounds may optionally also be present in microencapsulated form with one or more of the abovementioned excipients.

Suppositories may contain the customary water-soluble or water-insoluble excipients, for example polyethylene glycols, fats, for example cocoa fat, and higher esters (for example $C_{14}$ alcohol with $C_{16}$ fatty acid) or mixtures of these substances, in addition to the active compound or compounds.

Ointments, pastes, creams and gels may contain the customary excipients, for example animal and vegetable fats, waxes, paraffins, starch, tragacanth, cellulose derivatives, polyethylene glycols, silicones, bentonites, silica, talc and zinc oxide or mixtures of these substances, in addition to the active compound or compounds.

Powders and sprays may contain the customary excipients, for example lactose, talc, silica, alumina, calcium silicate and polyamide powder or mixtures of these substances, and sprays may additionally contain the customary propellants, for example chlorofluorohydrocarbons, in addition to the active compound or compounds.

Solutions and emulsions may contain the customary excipients such as solvents, solution retardants and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, maize germ oil, olive oil, castor oil and sesame oil, glycerol, glycerol formal, tetrahydrofurfuryl alcohol, polyethylene glycols and fatty acid esters of sorbitan or mixtures of these substances, in addition to the active compound or compounds.

For parenteral administration, the solutions and emulsions may also be present in sterial and blood-isotonic form.

Suspension may contain the customary excipients, such as liquid diluents, for example water, ethyl alcohol, propyl alcohol, suspending agents, for example ethoxylated isostearyl alcohols, polyoxyethylene sorbitol and sorbitan esters, microcrystalline cellulose, aluminum metahydroxide, bentonite, agar-agar and tragacanth or mixture of these substances, in addition to the active compound or compounds.

The formulation forms mentioned may also contain colorants, preservatives and odor-enhancing and flavor-enhancing additives, for example peppermint oil and eucalyptus oil and sweeteners, for example saccharin.

The therapeutically active compounds should preferably be present in the abovementioned pharmaceutical preparations in a concentration of about 0.1 to 99.5, preferably 0.5 to 95% by weight of the total mixture.

The abovementioned pharmaceutical preparations may also contain other pharmaceutical active compounds in addition to the active compounds according to the invention.

The abovementioned pharmaceutical preparations are prepared in a customary manner by known methods, for example by mixing the active compound or compounds with the excipient or excipients.

The present invention also includes the use of the active compounds according to the invention, and also pharmaceutical preparations which contain one or more active compounds according to the invention, in human and veterinary medicine for the prevention, amelioration and/or cure of the abovementioned disorders.

The active compounds or the pharmaceutical preparations may be administered locally, orally, parenterally, intraperitoneally and/or rectally, preferably parenterally, in particular intravenously.

In general, it has proved advantageous both in human and in veterinary medicine to administer the active compound or compounds according to the invention in total amounts of about 2.5 to about 200, preferably 5 to 150 mg/kg of body weight every 24 hours, if desired in the form of a number of individual doses in order to attain the desired results.

With oral administrations, the active compounds according to the invention are administered in total amounts of about 2.5 to about 200, preferably 5 to 150 mg/kg of body weight every 24 hours and with parenteral administration in total amounts of about 2.5 to about 50, preferably 1 to 25 mg/kg of body weight every 24 hours.

However, it may be necessary to depart from the dosages mentioned depending on the species and body weight of the subject to be treated, the nature and severity of the disease, the type of the preparation and the administration of the medicament and the time period or interval within which the administration takes place. Thus, in some cases it may be sufficient to manage with less than the abovementioned amount of active compound, whereas in other cases the abovementioned amount of active compound must be exceeded. The optimum dosage required in each case and the manner of administration of the active compounds can easily be determined by any person skilled in the art on the basis of his expert knowledge.

PREPARATION EXAMPLES

EXAMPLE 1

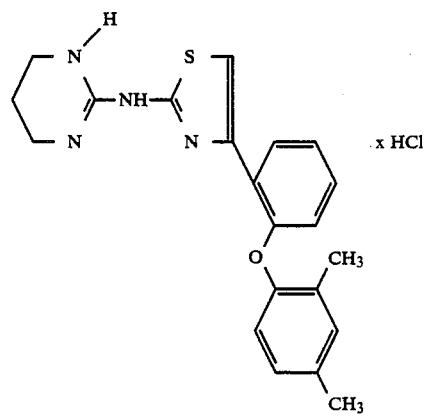

15.8 g (0.12 mol) of N-(1,4,5,6-tetrahydropyrimidinyl)thiourea (compare, for example, German Offenlegungsschrift No. 3,220,118) are added to 27.45 g (0.1 mol) of 2-(2,4-dimethylphenoxy)phenacyl chloride in 100 ml of acetone, the mixture is heated at reflux temperature for 2 hours and cooled, and the precipitated product is filtered off with suction, washed with acetone and dried.

37.8 g (91.4% of theory) of 4-[2-(2,4-dimethylphenoxy)phenyl]-2-[2-(1,4,5,6-tetrahydropyrimidinylamino]-thiazole hydrochloride of melting point 160° C. are obtained.

EXAMPLE 2

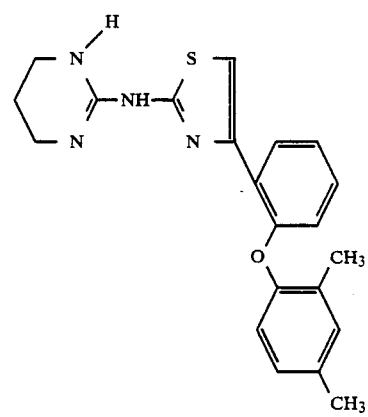

20.72 g (0.05 mol) of 4-[2-(2,4-dimethylphenoxy)-phenyl]2-[2-(1,4,5,6-tetrahydropyrimidinyl)amino]-thiazole hydrochloride are stirred at room temperature for 30 minutes with 300 ml of 1N sodium hydroxide solution. The insoluble solid is filtered off with suction, washed with water until neutral and dried.

16.2 g (86% of theory) of 4-[2-(2,4-dimethylphenoxy)phenyl]-2-[2-(1,4,5,6-tetrahydropyrimidinyl)amino]-thiazole of melting point 191°-192° C. are obtained.

Example 3

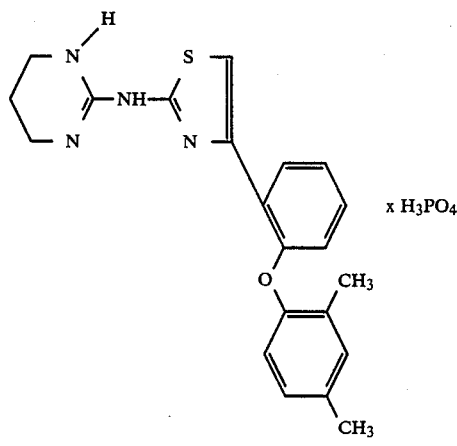

x H₃PO₄

4.72 g (0.041 mol) of 85% strength phosphoric acid are added to 15.12 g (0.04 mol) of 4-[2-(2,4-dimethyl-phenoxy)phenyl]-2-[2-(1,4,5,6-tetrahydropyrimidinyl-)amino]thiazole in 200 ml of ethanol, the mixture is heated at reflux temperature for 1 hour and cooled, and precipitated solid is filtered off with suction, washed with petroleum ether and dried.

18.66 g (98% of theory) of 4-[2-(2,4-dimethylphenoxy)phenyl]-2-[2-(1,4,5,6-tetrahydropyrimidinyl)amino]-thiazole dihydrogen phosphate of melting point 218° C. are obtained.

The following substituted 2-aminothiazoles of the general formula (I)

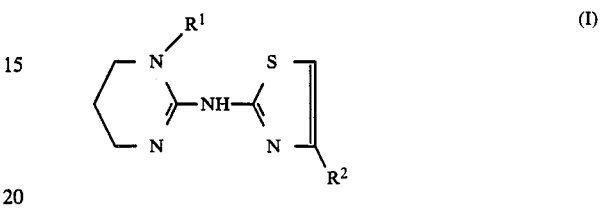

(I)

are obtained in a corresponding manner and according to the general instructions for preparation:

| Ex. No. | R¹ | R² | Acid addition salt with | Melting point/°C. |
|---|---|---|---|---|
| 4 | H | 2,6-dimethyl-4-(4-nitrophenoxy)phenyl | — | 246–247 |
| 5 | H | 4-(4-chlorophenoxy)phenyl | HBr | 244–245 |
| 6 | H | 3-(4-chlorophenoxy)phenyl | HBr | 168–170 |
| 7 | H | 4-(phenylthio)phenyl | HBr | 200–201 |
| 8 | H | 4-(phenylthio)phenyl | saccharin | 233–234 |
| 9 | H | 4-(phenylthio)phenyl | p-toluenesulfonic acid | 200–201 |
| 10 | H | 4-(4-chlorophenylthio)phenyl | HCl | 236–237 |

-continued

| Ex. No. | R¹ | R² | Acid addition salt with | Melting point/°C. |
|---|---|---|---|---|
| 11 | H | 4-methylphenyl-O-(2,4-dichlorophenyl) | HBr | 240–242 |
| 12 | H | 4-methylphenyl-O-(2,4-dichlorophenyl) | — | 167–169 |
| 13 | H | 4-methylphenyl-O-(2,6-dichloro-4-nitrophenyl) | HCl | 285–287 |
| 14 | H | 2-methylphenyl-O-(2,4-dichlorophenyl) | HBr | 207–208 |
| 15 | H | 2-methylphenyl-O-(2,4-dimethylphenyl) | HBr | 212–214 |
| 16 | H | 2-methylphenyl-O-(2,4-dichlorophenyl) | CH₃—SO₃H | 197–198 |
| 17 | H | 2-methylphenyl-O-phenyl | HBr | 229–230 |
| 18 | H | 2-methylphenyl-O-phenyl | — | 199–200 |
| 19 | H | 2-methylphenyl-O-phenyl | HCl | 214–215 |
| 20 | H | 2-methylphenyl-O-phenyl | saccharin | 225–226 |

-continued

| Ex. No. | R¹ | R² | Acid addition salt with | Melting point/°C. |
|---|---|---|---|---|
| 21 | H | 2-methylphenyl phenyl ether | 4-CH₃-C₆H₄-SO₃H | 174–175 |
| 22 | H | 2-methylphenyl phenyl ether | CH₃—SO₃H | 277–279 |
| 23 | H | 4-chloro-2-methylphenyl 4-chlorophenyl ether | HBr | 240–241 |
| 24 | H | 2,4-dimethylphenyl 3-methylphenyl ether | HBr | 106–107 |
| 25 | H | 2,4-dimethylphenyl phenyl ether | HBr | 227–228 |
| 26 | H | 4-methylphenyl phenyl ether | HBr | 219 |
| 27 | H | 4-methylphenyl 4-tert-butylphenyl sulfide | HBr | 166–168 |
| 28 | H | bis(4-methylphenyl) sulfide | HBr | 218–220 |
| 29 | H | 4-methylphenyl 4-chloro-2-methylphenyl ether | HBr | 248–250 |
| 30 | H | 2-methylphenyl 2,3-dimethylphenyl ether | CH₃—SO₃H | 217 |
| 31 | H | 4-nitro-2-methylphenyl 4-methylphenyl ether | HCl | 290–292 |

-continued
| Ex. No. | R¹ | R² | Acid addition salt with | Melting point/°C. |
|---|---|---|---|---|
| 32 | H | 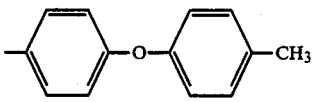 | HBr | 227–229 |
| 33 | H | 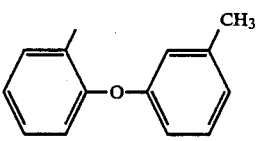 | HBr | 253–254 |
| 34 | H | 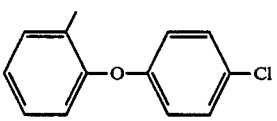 | HBr | 244–245 |
| 35 | H | 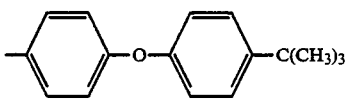 | HBr | 241–243 |
| 36 | H | 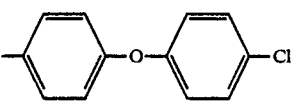 | HBr | 165–167 |
| 37 | H | 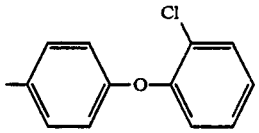 | HBr | 230–231 |
| 38 | H | 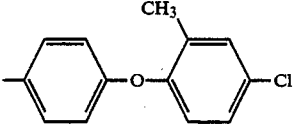 | HBr | 263–264 |
| 39 | H | 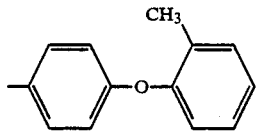 | HBr | 211–213 |
| 40 | H | 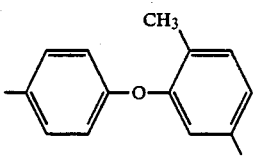 | HBr | 236–238 |
| 41 | H | 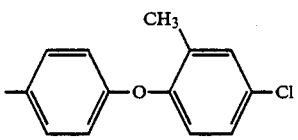 | HBr | 193–195 |
| 42 | H | 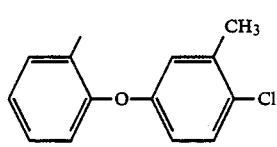 | HBr | 248–249 |

-continued

| Ex. No. | R¹ | R² | Acid addition salt with | Melting point/°C. |
|---|---|---|---|---|
| 43 | H | 2-methylphenyl-O-3-chlorophenyl | HBr | 249–250 |
| 44 | H | 2-methylphenyl-O-4-tert-butylphenyl | HCl | 189–190 |
| 45 | H | 2-methylphenyl-O-(2-methyl-4-chlorophenyl) | HBr | 232–233 |
| 46 | H | 2-methylphenyl-O-(2-methyl-4-chlorophenyl) | HCl | 238 |
| 47 | H | 2-methylphenyl-O-(2-methyl-4-chlorophenyl) | $CH_3-SO_3H$ | 216–217 |
| 48 | H | 2-methylphenyl-O-(2-methyl-3-chlorophenyl) | HBr | 265–266 |
| 49 | H | 2-methylphenyl-O-(2-methyl-3-chlorophenyl) | HCl | 216 |
| 50 | H | 2-methylphenyl-O-(2-methyl-3-chlorophenyl) | $CH_3-SO_3H$ | 228–229 |
| 51 | H | (2-methyl-4-fluorophenyl)-O-(4-fluorophenyl) | HBr | 286–287 |
| 52 | H | (2-methyl-4-fluorophenyl)-O-(4-fluorophenyl) | HCl | 273–274 |
| 53 | H | (2-methyl-4-fluorophenyl)-O-(4-fluorophenyl) | $CH_3-SO_3H$ | 235–236 |

-continued
| Ex. No. | R¹ | R² | Acid addition salt with | Melting point/°C. |
|---|---|---|---|---|
| 54 | H | 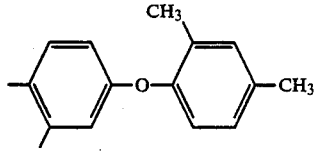 | — | 228–229 |
| 55 | H | 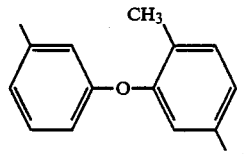 | HBr | 229–230 |
| 56 | H | 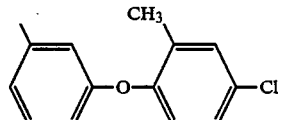 | HBr | 277–278 |
| 57 | H | 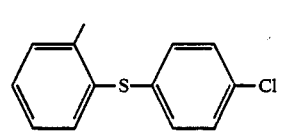 | HBr | 200 |
| 58 | H | 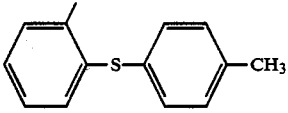 | HBr | 216 |
| 59 | H | 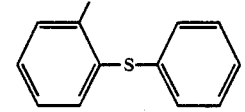 | HBr | 144 |
| 60 | H | 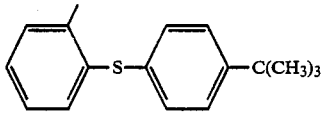 | — | 201 |
| 61 | H | 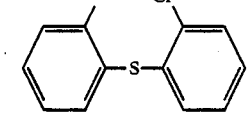 | HBr | 199–200 |
| 62 | H | 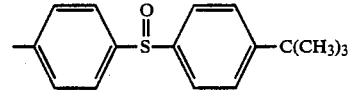 | HBr | 162 |
| 63 | H | 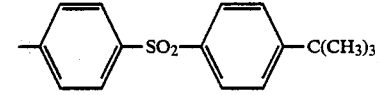 | HBr | 255–256 |
| 64 | H | 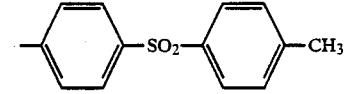 | HBr | 283–284 |

-continued

| Ex. No. | R[1] | R[2] | Acid addition salt with | Melting point/°C. |
|---|---|---|---|---|
| 65 | H | 4-(phenylsulfonyl)phenyl (–C6H4–SO2–C6H5) | HBr | 286–287 |
| 66 | H | 3-methylphenyl phenyl sulfide (3-CH3-C6H4–S–C6H5) | — | 214 |
| 67 | H | 3-methylphenyl 4-methylphenyl sulfide | HBr | 225 |
| 68 | H | 3-methylphenyl 4-tert-butylphenyl sulfide | — | 199 |
| 69 | H | 2-methylphenyl phenyl ether | CH3—SO3H | >250 |
| 70 | H | 4-methylphenyl phenyl ether | CH3—SO3H | 203 |
| 71 | H | 2-methylphenyl 2,4-difluorophenyl ether | HCl | 236 |
| 72 | H | 2-methylphenyl 2,4-difluorophenyl ether | — | 199 |
| 73 | H | 2-methylphenyl 2,4-difluorophenyl ether | CH3—SO3H | 220–222 |
| 74 | H | 4-methylphenyl 4-(trifluoromethyl)phenyl ether | HCl | >250 |
| 75 | H | 4-methylphenyl 4-(trifluoromethyl)phenyl ether | — | 22–223 |

-continued
| Ex. No. | R¹ | R² | Acid addition salt with | Melting point/°C. |
|---|---|---|---|---|
| 76 | H | 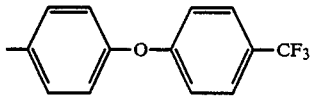 | CH₃—SO₃H | 207 |
| 77 | H | 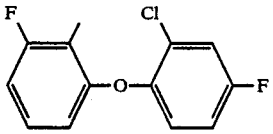 | HCl | 172 |
| 78 | H | 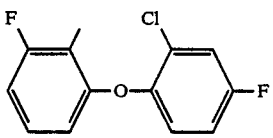 | — | 168 (decomp.) |
| 79 | H | 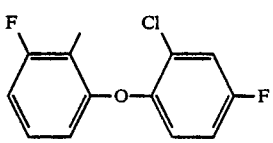 | CH₃—SO₃H | 169 (decomp.) |
| 80 | H | 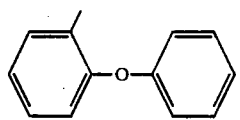 | 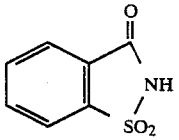 | 216 |
| 81 | H | 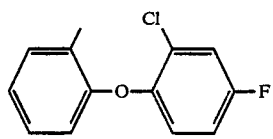 | HCl | 188 |
| 82 | H | 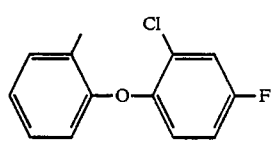 | — | 234–235 |
| 83 | H | 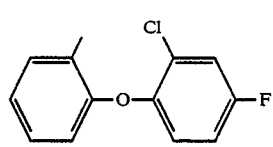 | CH₃—SO₃H | 234 |
| 84 | H | 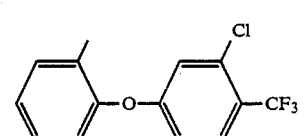 | — | 124–125 |
| 85 | H | 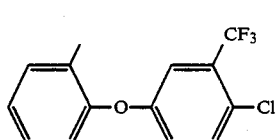 | — | 128 (decomp.) |
| 86 | H | 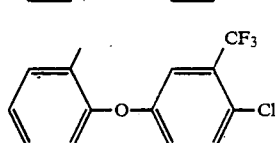 | CH₃—SO₃H | 240 |

-continued

| Ex. No. | R¹ | R² | Acid addition salt with | Melting point/°C. |
|---|---|---|---|---|
| 87 | H | 2-methyl-phenyl-O-(3-CF₃-phenyl) | HCl | 172 |
| 88 | H | 2-methyl-phenyl-O-(3-CF₃-phenyl) | — | 158 |
| 89 | H | 2-methyl-phenyl-O-(3-CF₃-phenyl) | $CH_3\text{—}SO_3H$ | 135 (decomp.) |
| 90 | H | 2-methyl-phenyl-O-(2-$C_2H_5$-phenyl) | HCl | 136 |
| 91 | H | 2-methyl-phenyl-O-(2-$C_2H_5$-phenyl) | — | 149 |
| 92 | H | 2-methyl-phenyl-O-(2-$C_2H_5$-phenyl) | $CH_3\text{—}SO_3H$ | 164 |
| 93 | H | 2-methyl-phenyl-O-(2-$OCH_3$-phenyl) | HCl | 250–252 |
| 94 | H | 2-methyl-phenyl-O-(2-$OCH_3$-phenyl) | — | 240 |
| 95 | H | 2-methyl-phenyl-O-(2-$OCH_3$-phenyl) | $CH_3\text{—}SO_3H$ | 230 (decomp.) |
| 96 | H | 2-methyl-phenyl-O-(1-naphthyl) | HCl | 220 |

-continued
| Ex. No. | R¹ | R² | Acid addition salt with | Melting point/°C. |
|---|---|---|---|---|
| 97 | H | 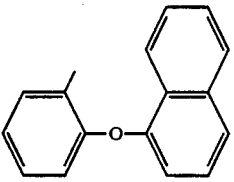 | — | 223 |
| 98 | H | 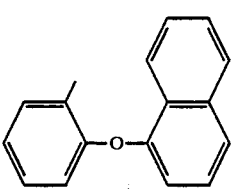 | $CH_3$—$SO_3H$ | >250 |
| 99 | H | 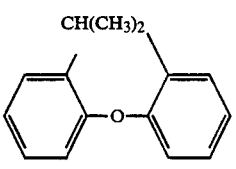 | HCl | 134–135 |
| 100 | H | 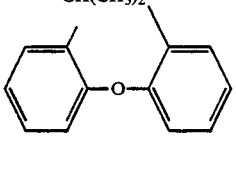 | — | 225 |
| 101 | H | 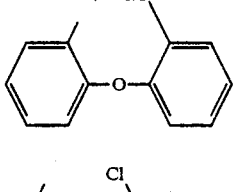 | $CH_3$—$SO_3H$ | 162 |
| 102 | H | 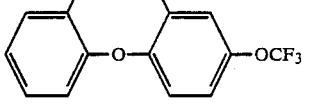 | HCl | 138 |
| 103 | H | 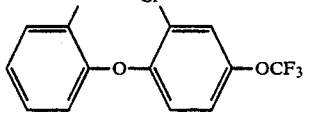 | — | 205 |
| 104 | H | 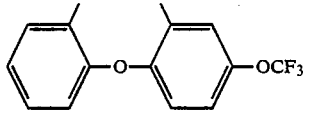 | $CH_3$—$SO_3H$ | 208 |
| 105 | H | 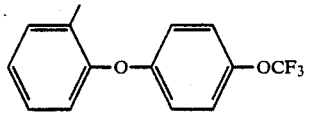 | HCl | 162 |

-continued
| Ex. No. | R¹ | R² | Acid addition salt with | Melting point/°C. |
|---|---|---|---|---|
| 106 | H | 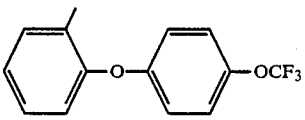 | — | 173 |
| 107 | H | 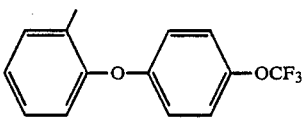 | CH₃—SO₃H | 220 |
| 108 | H | 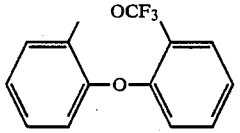 | HCl | 196 |
| 109 | H | 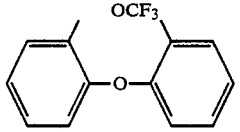 | — | 155 |
| 110 | H | 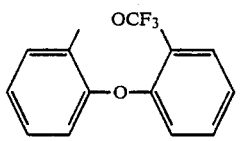 | CH₃—SO₃H | 196 |
| 111 | H | 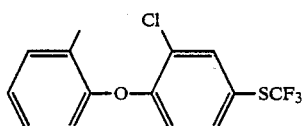 | HCl | 250–251 |
| 112 | H | 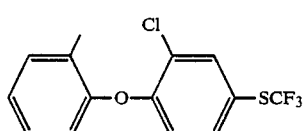 | — | 238 |
| 113 | H | 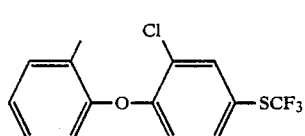 | CH₃—SO₃H | 176 (decomp.) |
| 114 | H | 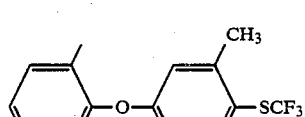 | HCl | 127 |
| 115 | H | 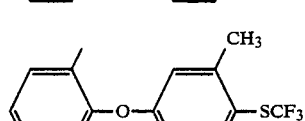 | — | 134 |
| 116 | H | 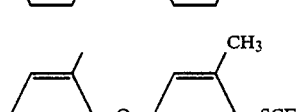 | CH₃—SO₃H | 217 |

-continued

| Ex. No. | R¹ | R² | Acid addition salt with | Melting point/°C |
|---|---|---|---|---|
| 117 | H | 2-(2-methylphenoxy)phenyl-cyclohexyl | HCl | 150 (decomp.) |
| 118 | H | 2-(2-methylphenoxy)phenyl-cyclopentyl | — | 145–146 |
| 119 | H | 2-(2-methylphenoxy)phenyl-cyclopentyl | CH₃—SO₃H | 177 |
| 120 | H | 4-fluoro-2,3-dimethyl-(2-methylphenoxy)phenyl | — | 235–237 |
| 121 | H | 4-fluoro-2,3-dimethyl-(2-methylphenoxy)phenyl | — | 235–237 |
| 122 | H | 4-fluoro-2,3-dimethyl-(2-methylphenoxy)phenyl | CH₃—SO₃H | >250 |
| 123 | H | 2-methylphenoxy-phenyl | CH₃—CH(OH)—COOH | 179 |

| Ex. No. | R¹ | R² | Acid addition salt with | Melting point/°C |
|---|---|---|---|---|
| 124 | H | 2-methylphenoxy-phenyl | HOOC—CH₂—CH₂—COOH | 160 |

-continued
| Ex. No. | R¹ | R² | Acid addition salt with | Melting point/°C. |
|---|---|---|---|---|
| 125 | H | 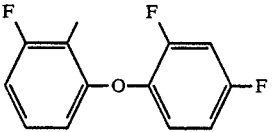 | — | 103–105 (decomp.) |
| 126 | H | 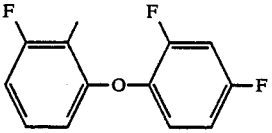 | CH₃—SO₃H | 107 (decomp.) |
| 127 | H | 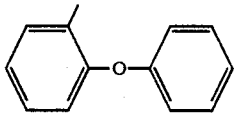 | HOOC—CH₂—C(OH)(COOH)—CH₂—COOH | 112 |
| 128 | H | 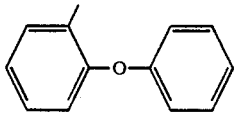 | CH₃—(CH₂)₇—CH=CH—(CH₂)₇—COOH | 169 |
| 129 | H | 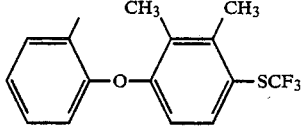 | HCl | 156 |
| 130 | H | 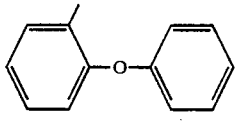 | HOOC—(CH₂)₄—COOH | 109 |
| 131 | H | 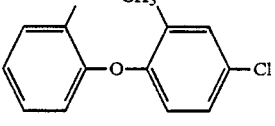 | CH₃—SO₃H | 215 |
| 132 | H | 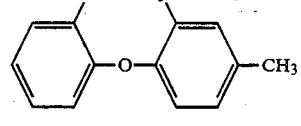 | HOOC—CH₂—C(OH)(COOH)—CH₂—COOH | 192 (decomp.) |
| 133 | H | 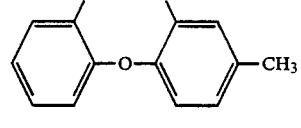 | CH₃—CH(OH)—COOH | 126 |
| 134 | H | 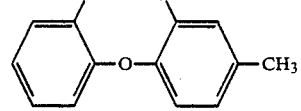 | HOOC—CH₂—CH₂—COOH | 150 (decomp.) |

-continued
| Ex. No. | R¹ | R² | Acid addition salt with | Melting point/°C |
|---|---|---|---|---|
| 135 | H | 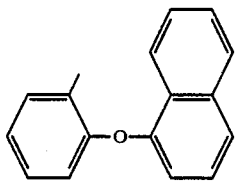 | HOOC—CH$_2$—C(OH)(COOH)—CH$_2$—COOH | 173 (decomp.) |
| 136 | H | 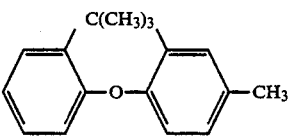 | — | 232° C. |
| 137 | H | 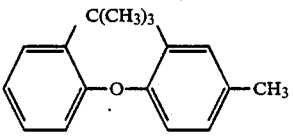 | CH$_3$—SO$_3$H | >250 |
| 138 | H | 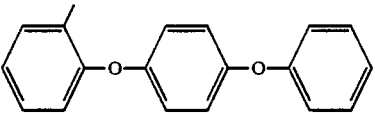 | HCl | 128 |
| 139 | H | 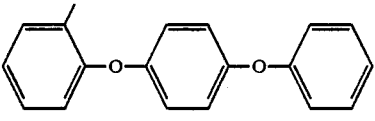 | — | 159 |
| 140 | H | 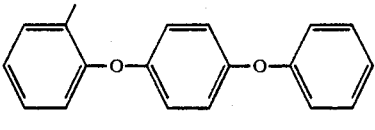 | CH$_3$—SO$_3$H | 218 |
| 141 | H | 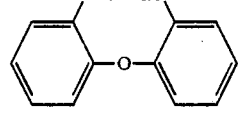 | — | 240 |
| 142 | H | 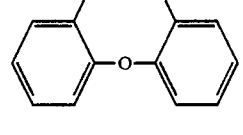 | CH$_3$—SO$_3$H | 210 (decomp.) |
| 143 | H | 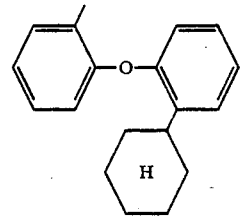 | — | 198 |

-continued

| Ex. No. | R¹ | R² | Acid addition salt with | Melting point/°C. |
|---|---|---|---|---|
| 144 | H | 2-methylphenoxy-naphthalen-1-yl (1-(2-methylphenoxy)naphthalene) | — | >250 |
| 145 | H | 2-(2-methylphenoxy)phenyl-cyclohexyl | $CH_3-SO_3H$ | 180 |
| 146 | H | 4-(2-methylphenoxy)-2-methyl-1-(SCF₃)phenyl | $HOOC-CH_2-\underset{\underset{OH}{\mid}}{CH}-CH_2-COOH$ | 158 |
| 147 | H | 4-(2-methylphenoxy)-2-methyl-1-(SCF₃)phenyl | $CH_3-\underset{\underset{OH}{\mid}}{CH}-COOH$ | 137 |
| 148 | H | 2',4-dimethylbiphenyl | $C_2H_5O-SO_3H$ | 215 |
| 149 | H | 4-(2-methylphenoxy)-2,4-dimethylphenyl | $HNO_3$ | 193 (decomp.) |
| 150 | H | 4-(2-methylphenoxy)-2,4-dimethylphenyl | $H_2SO_4$ | 245 |
| 151 | H | 1-(2-methylphenoxy)naphthalen-yl | $CH_3-\underset{\underset{OH}{\mid}}{CH}-COOH$ | 200 (decomp.) |
| 152 | H | 1-(2-methylphenoxy)naphthalen-yl | — | 222 |

-continued

| Ex. No. | R¹ | R² | Acid addition salt with | Melting point/°C. |
|---|---|---|---|---|
| 153 | H | 2-(2-methylphenoxy)naphthalene | CH₃—SO₃H | 195 |
| 154 | H | 2-methylphenyl 2-(sec-butyl)phenyl ether (CH(CH₃)-C₂H₅) | HCl | 113 |
| 155 | H | 2-methylphenyl 2-(sec-butyl)phenyl ether (CH(CH₃)-C₂H₅) | — | 130 |
| 156 | H | 2-methylphenyl 4-chloro-2-methylphenyl ether | HNO₃ | 130 (decomp.) |
| 157 | H | 2-methylphenyl 4-chloro-2-methylphenyl ether | CH₃—CH(OH)—COOH | 212 |
| 158 | H | 2-methylphenyl 3-phenoxyphenyl ether | — | 89 |
| 159 | H | 2-methylphenyl 2-(sec-butyl)phenyl ether (CH(CH₃)-C₂H₅) | CH₃—SO₃H | 158 |
| 160 | H | 2-methylphenyl 3-phenoxyphenyl ether | CH₃—SO₃H | 114 |
| 161 | H | 2-methylphenyl 4-biphenylyl ether | HCl | 228–229 |

-continued
| Ex. No. | R¹ | R² | Acid addition salt with | Melting point/°C. |
|---|---|---|---|---|
| 162 | H | 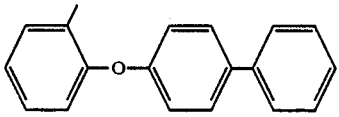 | — | 222 |
| 163 | H | 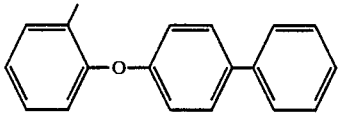 | $CH_3-SO_3H$ | 221 |
| 164 | $CH_3$ | 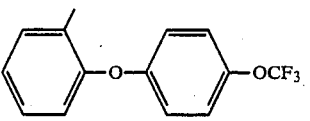 | HCl | 173–174 |
| 165 | $CH_3$ | 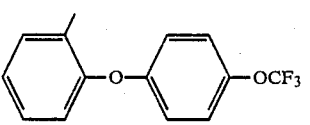 | $CH_3-SO_3H$ | |
| 166 | $CH_3$ | 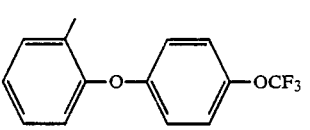 | — | 196 (decomp.) |
| 167 | $CH_3$ | 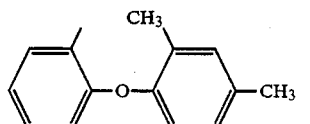 | HCl | 119–120 |
| 169 | $CH_3$ | 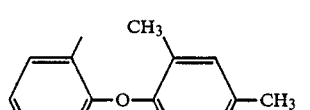 | — | 116 |
| 169 | $CH_3$ | 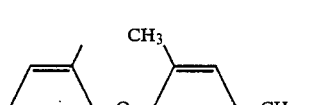 | $CH_3-SO_3H$ | 143 (decomp.) |
| 170 | H | 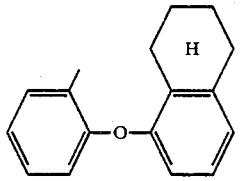 | — | 240 (decomp.) |
| 171 | H | 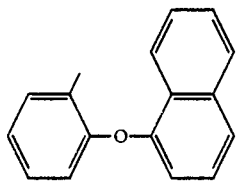 | $H_3PO_4$ | 122 |

-continued
| Ex. No. | R¹ | R² | Acid addition salt with | Melting point/°C. |
|---|---|---|---|---|
| 172 | H | 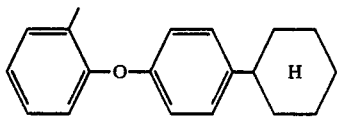 | HCl | 170–171 |
| 173 | CH₃ | 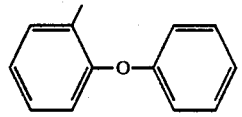 | HBr | 263 |
| 174 | CH₃ | 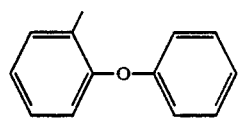 | — | 226 |
| 175 | CH₃ | 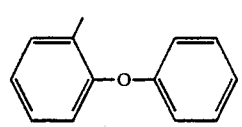 | CH₃—SO₃H | 138 |
| 176 | H | 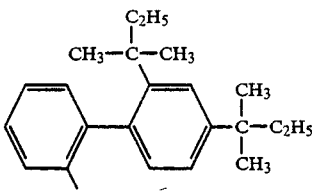 | — | 187 |
| 177 | H | 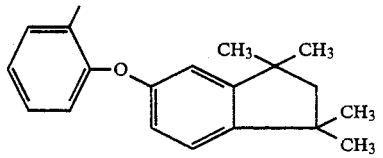 | — | 160 |
| 178 | H | 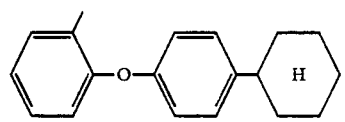 | — | 208–210 |
| 179 | CH₃ | 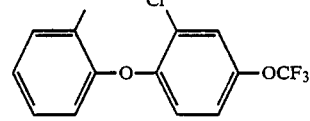 | HCl | 192 |
| 180 | CH₃ | 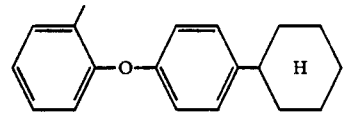 | — | 162 |
| 181 | H | 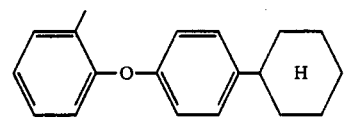 | CH₃—SO₃H | >250 |

-continued

| Ex. No. | R¹ | R² | Acid addition salt with | Melting point/°C. |
|---|---|---|---|---|
| 182 | CH₃ | 2-methylphenyl-O-(2-chloro-4-trifluoromethoxyphenyl) | — | 203 |
| 183 | CH₃ | 2-methylphenyl-O-(4-cyclohexylphenyl), H | HCl | 165–166 |
| 184 | CH₃ | 2-methylphenyl-O-(2-chloro-4-trifluoromethoxyphenyl) | CH₃—SO₃H | 165 |
| 185 | H | 2-methylphenyl-(2-(3-pentyl)-4-(3-methylpent-3-yl)phenyl) | CH₃—SO₃H | 188 |
| 186 | H | 2-methylphenyl-S-phenyl | — | 140 |
| 187 | H | 2-methylphenyl-S-(2-methyl-4-methylphenyl) | HBr | 212–214 |
| 188 | CH₃ | 2-methylphenyl-S-phenyl | HBr | 242–244 |
| 189 | H | 2-methylphenyl-S-(2-methyl-4-methylphenyl) | — | 215 |
| 190 | CH₃ | 2-methylphenyl-S-phenyl | — | 225 |
| 191 | H | 2-methylphenyl-S-phenyl | H₃PO₄ | 140 |

-continued

| Ex. No. | R¹ | R² | Acid addition salt with | Melting point/°C. |
|---|---|---|---|---|
| 192 | CH₃ | (2-methylphenyl)(phenyl)sulfide | H₃PO₄ | 228 |
| 193 | H | (2-methylphenyl)(2,4-dimethylphenyl)sulfide | H₃PO₄ | 201 |
| 194 | H | 2-methylphenyl 2-biphenylyl ether | — | 221 |
| 195 | H | 2-methylphenyl 4-(2-phenylpropan-2-yl)phenyl ether | HCl | 212 (decomp.) |
| 196 | H | 2-methylphenyl 4-(2-phenylpropan-2-yl)phenyl ether | — | 208 |
| 197 | H | 2-methylphenyl 2-biphenylyl ether | H₃PO₄ | 152 |

-continued
| Ex. No. | R¹ | R² | Acid addition salt with | Melting point/°C. |
|---|---|---|---|---|
| 198 | H | 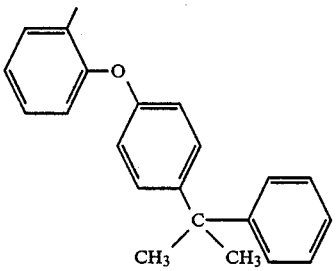 | H₃PO₄ | 205 |
| 199 | H | 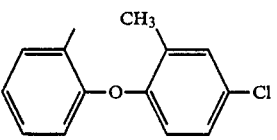 | HCl | >250 |
| 200 | H | 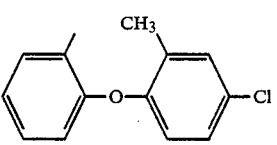 | — | >250 |
| 201 | H | 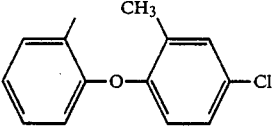 | H₃PO₄ | 255 |
| 202 | H | 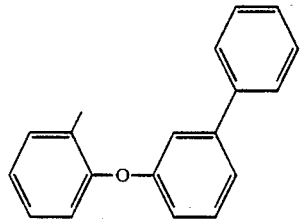 | HCl | 212 |
| 203 | H | 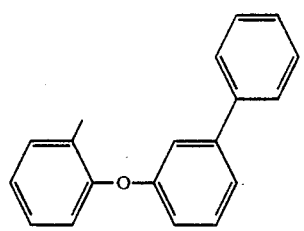 | — | 208 |
| 204 | H | 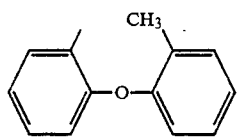 | HCl | 220 |
| 205 | H | 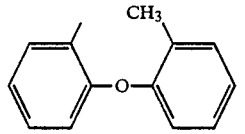 | — | 225–227 |

-continued

| Ex. No. | R¹ | R² | Acid addition salt with | Melting point/°C. |
|---|---|---|---|---|
| 206 | H | 2-(3-phenylphenoxy)toluene | $H_3PO_4$ | 115 |
| 207 | H | 4-(2-methylphenoxy)-1,2-dimethylbenzene | HCl | 131 |
| 208 | H | 4-(2-methylphenoxy)-1,2-dimethylbenzene | — | 192 |
| 209 | H | bis(2-methylphenyl) ether | $H_3PO_4$ | 225 |
| 210 | H | 4-(2-methylphenoxy)-1,2-dimethylbenzene | $H_3PO_4$ | 133 (decomp.) |
| 211 | H | 2-methylphenyl phenyl sulfone | — | 212–214 |
| 212 | H | 2-methylphenyl phenyl sulfone | $H_3PO_4$ | 198 |
| 213 | H | 2-ethyl-4-methylphenyl 2-methylphenyl ether | — | 148 |
| 214 | H | 2-ethyl-5-methylphenyl 2-methylphenyl ether | HCl | 236 |

-continued

| Ex. No. | R¹ | R² | Acid addition salt with | Melting point/°C. |
|---|---|---|---|---|
| 215 | H | 2-(2-methylphenoxy)-1-ethyl-4-methylbenzene structure | — | 245 |
| 216 | H | 2-(2-methylphenoxy)-1-ethyl-4-methylbenzene structure | $H_3PO_4$ | 233 |
| 217 | H | 2-(2-methylphenoxy)-1-ethyl-5-methylbenzene structure | $H_3PO_4$ | 149 |
| 218 | H | 2-(2-methylphenoxy)-1,3-dimethylbenzene structure | — | 240 |
| 219 | H | 2-(2-methylphenoxy)-1,3-dimethylbenzene structure | $H_3PO_4$ | 192 |
| 220 | H | 2-(2-methylphenoxy)-1,3-dimethyl-4-SCF₃ benzene structure | — | 198 |
| 221 | H | 2-(2-methylphenoxy)-1,3-dimethyl-4-SCF₃ benzene structure | $H_3PO_4$ | 180 |
| 222 | H | 2-(2-methylphenoxy)-1-ethyl-5-methylbenzene structure | $H_2SO_4$ | 196 |
| 223 | H | 2-(2-methylphenoxy)-1-ethyl-5-methylbenzene structure | $HNO_3$ | 155 |
| 224 | H | 2-(2-methylphenoxy)-1-ethyl-5-methylbenzene structure | $CH_3-CH(OH)-COOH$ | oil |

-continued
| Ex. No. | R¹ | R² | Acid addition salt with | Melting point/°C. |
|---|---|---|---|---|
| 225 | H | 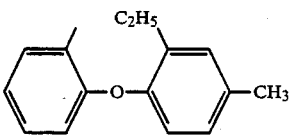 | HOOC—(CH₂)₂—COOH | 70 |
| 226 | H | 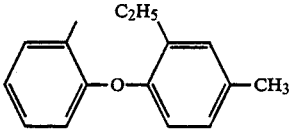 | HOOC—CH₂—C(OH)(COOH)—CH₂—COOH | 83 |
| 227 | H | 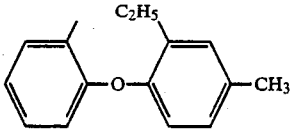 | CH₃—COOH | 56 |
| 228 | H | 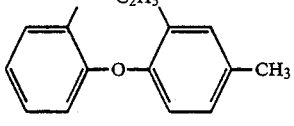 | HOOC—CH=CH—COOH (cis) | 153 |
| 229 | H | 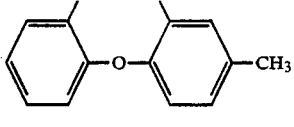 | HOOC—COOH | oil |
| 230 | H | 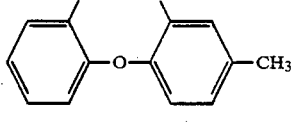 | HOOC—(CH₂)₃—COOH | 198 |
| 231 | H | 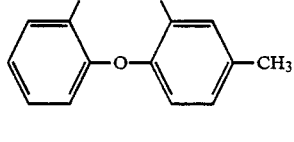 | HOOC—CH₂—CH(OH)—COOH | oil |
| 232 | H | 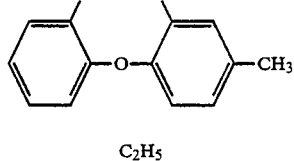 | HOOC—CH=CH—COOH (trans) | 182 |
| 233 | H | 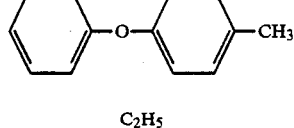 | HOOC—(CH₂)₄—COOH | oil |
| 234 | H | 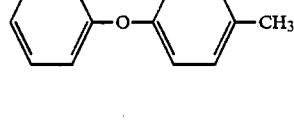 | HOOC—(CH₂)₇—CH=CH—(CH₂)₇—CH₃ | oil |

-continued

| Ex. No. | R¹ | R² | Acid addition salt with | Melting point/°C. |
|---|---|---|---|---|
| 235 | H | 2-methylphenoxy-(2-ethyl-4-methylphenyl) | 2-(sulfamoyl)benzamide derivative | 218 |

| Ex. No. | R¹ | R² | Acid addition salt with | Melting point/°C. |
|---|---|---|---|---|
| 236 | H | 2-methylphenoxy-(2-methyl-4-methylphenyl) | HOOC—CH=CH—COOH (cis) | 186 (decomp.) |
| 237 | H | 2-methylphenoxy-(2,3-dimethyl-4-SCF₃-phenyl) | — | 190 |
| 238 | H | 2-methylphenoxy-(2,3-dimethyl-4-SCF₃-phenyl) | H₃PO₄ | 199 (decomp.) |
| 239 | H | 2-methylphenoxy-(with CH₂—CH—SCF₃ and CH₃ substituents) | — | 195 |
| 240 | H | 2-methylphenoxy-(2-OCH₃-4-SCF₃-phenyl) | HCl | 171 |
| 241 | H | 2-methylphenoxy-(2-OCH₃-4-SCF₃-phenyl) | — | 164 |
| 242 | H | 2-methylphenoxy-(2,5-dimethyl-4-SCF₃-phenyl) | H₃PO₄ | 212 |
| 243 | H | 2-methylphenoxy-(2-OCH₃-4-SCF₃-phenyl) | H₃PO₄ | 190 |

-continued
| Ex. No. | R¹ | R² | Acid addition salt with | Melting point/°C. |
|---|---|---|---|---|
| 244 | H | 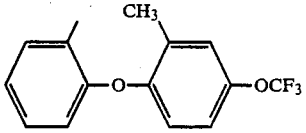 | HCl | 178 |
| 245 | H | 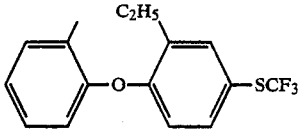 | — | 162 |
| 246 | H | 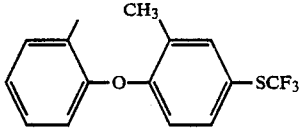 | HCl | 225–226 |
| 247 | H | 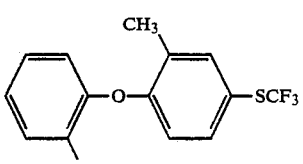 | — | 233 |
| 248 | H | 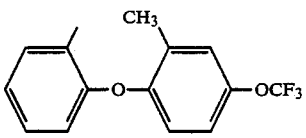 | — | 201 |
| 249 | H | 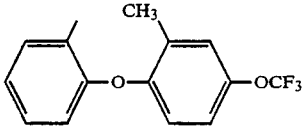 | $H_3PO_4$ | 190 |
| 250 | H | 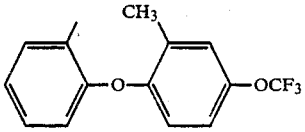 | $CH_3-CH-COOH$<br>    $\|$<br>    $OH$ | 112 |
| 251 | H | 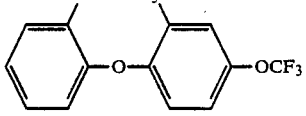 | $HOOC-(CH_2)_2-COOH$ | 132 |
| 252 | H | 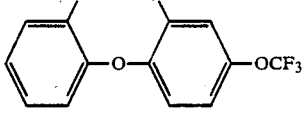 | $\phantom{HOOC-CH_2-}OH$<br>$HOOC-CH_2-\underset{\underset{COOH}{\|}}{C}-CH_2-COOH$ | 143 |
| 253 | H | 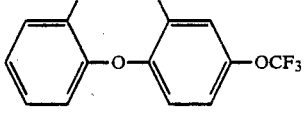 | $HOOC-CH$<br>$\phantom{HOOC-}\|\|$<br>$HOOC-CH$ (cis) | 180 (decomp.) |

-continued
| Ex. No. | R¹ | R² | Acid addition salt with | Melting point/°C. |
|---|---|---|---|---|
| 254 | H | 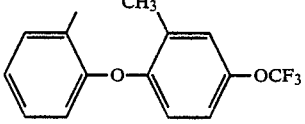 | HOOC—COOH | 98 |
| 255 | H | 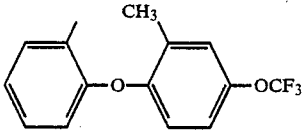 | HOOC—CH₂—CH—COOH<br>      \|<br>      OH | 138 |
| 256 | H | 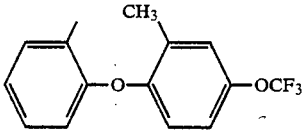 | CH—COOH<br> \|\|<br>HOOC—CH<br>(trans) | 112 |
| 257 | H | 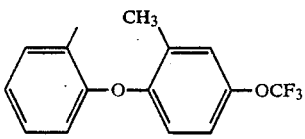 | HOOC—(CH₂)₄—COOH | 107 |
| 258 | H | 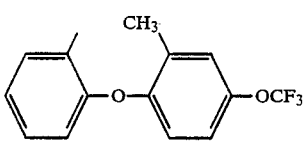 | 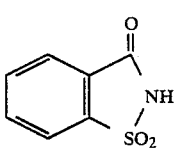 | 159 |
| 259 | H | 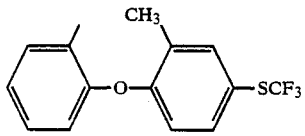 | H₃PO₄ | 110 (decomp.) |
| 260 | H | 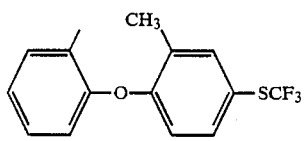 | CH₃—CH—COOH<br>      \|<br>      OH | 138 |
| 261 | H | 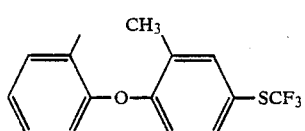 | CH₂—COOH<br>\|<br>HOOC—CH₂ | 151 |
| 262 | H | 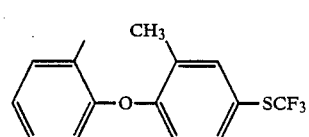 | OH<br>\|<br>HOOC—CH₂—C—CH₂—COOH<br>\|<br>COOH | 189 |
| 263 | H | 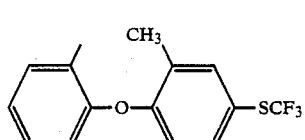 | HOOC—CH=CH—COOH<br>(cis) | 211 |
| 264 | H | 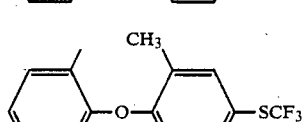 | HOOC—COOH | 238 |

-continued
| Ex. No. | R¹ | R² | Acid addition salt with | Melting point/°C. |
|---|---|---|---|---|
| 265 | H | 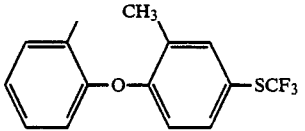 | HOOC—CH₂—CH(OH)—COOH | 220 (decomp.) |
| 266 | H | 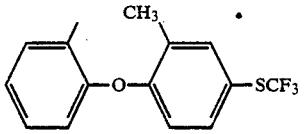 | HOOC—CH=CH—COOH (trans) | 189 |
| 267 | H | 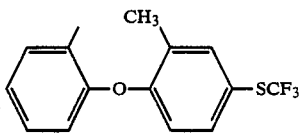 | HOOC—(CH₂)₄—COOH | 142 |
| 268 | H | 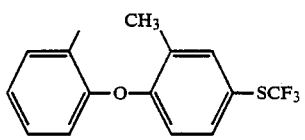 | 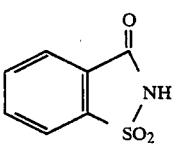 | 60 |
| 269 | H | 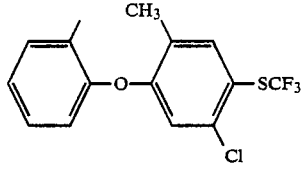 | HCl | 232 |
| 270 | H | 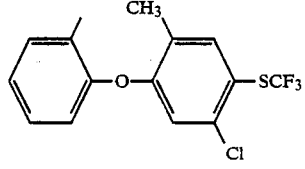 | — | 230–231 |
| 271 | H | 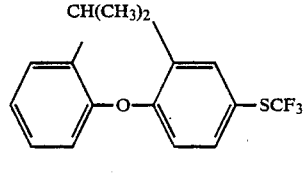 | HCl | 181 |
| 272 | H | 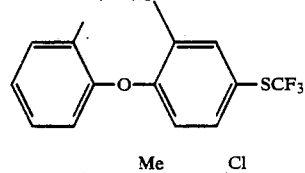 | — | 174–175 |
| 273 | H | 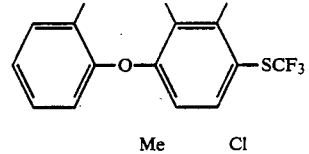 | HCl | 211 |
| 274 | H | 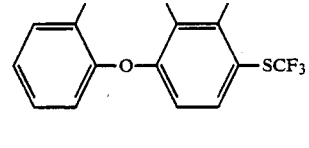 | — | 204–205 |

-continued
| Ex. No. | R¹ | R² | Acid addition salt with | Melting point/°C. |
|---|---|---|---|---|
| 275 | H | 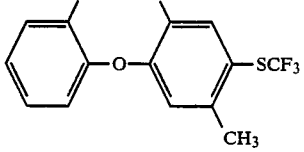 | HCl | oil |
| 276 | H | 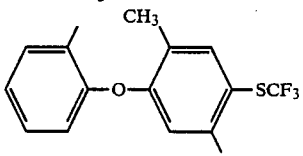 | — | 250 |
| 277 | H | 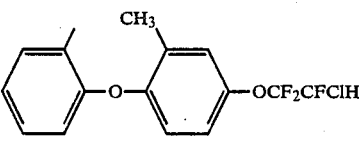 | HCl | 112 (decomp.) |
| 278 | H | 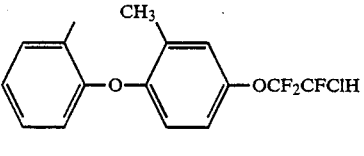 | — | 114 |
| 279 | H | 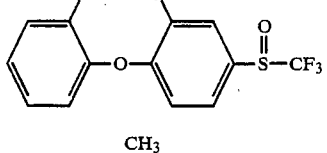 | HBr | 247–8 |
| 280 | H | 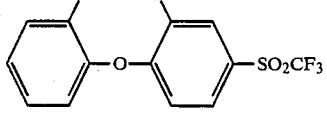 | HBr | >250 |
| 281 | H | 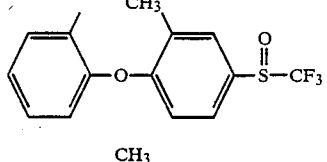 | — | 245 |
| 282 | H | 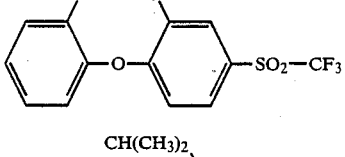 | — | >250 |
| 283 | H | 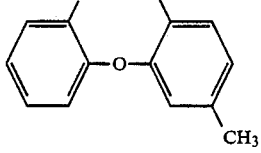 | — | CH₂— |
| 284 | H | 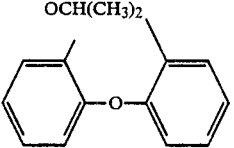 | — | 135 |

-continued
| Ex. No. | R¹ | R² | Acid addition salt with | Melting point/°C. |
|---|---|---|---|---|
| 285 | H | 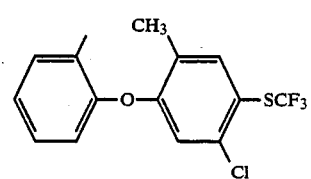 | HOOC—CH$_2$—CH—COOH<br>　　　　　　\|<br>　　　　　　OH | 179 (decomp.) |
| 286 | H | 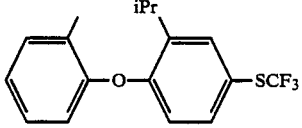 | HOOC—CH—HOOC—CH (cis)<br>　　　　\|<br>　　　　OH | 68 |
| 287 | H | 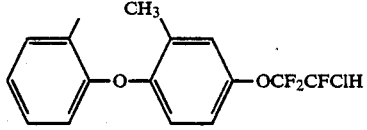 | | 34 |
| 288 | H | 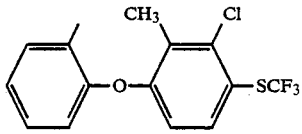 | HOOC—CH$_2$—CH—COOH<br>　　　　　　\|<br>　　　　　　OH | 62 |
| 289 | H | 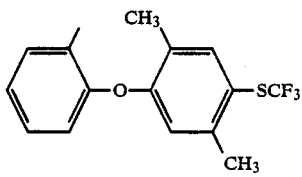 | HOOC—CH$_2$—CH—COOH<br>　　　　　　\|<br>　　　　　　OH | 130 |
| 290 | H | 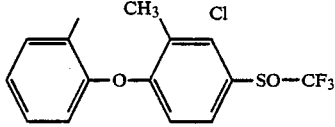 | HOOC—CH$_2$—CH—COOH<br>　　　　　　\|<br>　　　　　　OH | 142 |
| 291 | H | 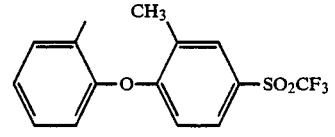 | HOOC—CH$_2$—CH—COOH<br>　　　　　　\|<br>　　　　　　OH | >250° C. |
| 292 | H | 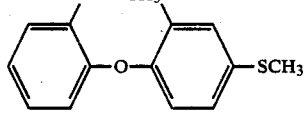 | HCl | oil |
| 293 | H | 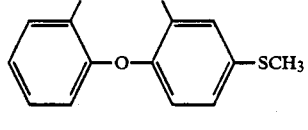 | — | oil |
| 294 | H | 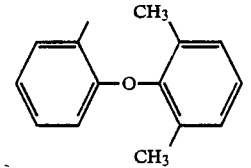 | HCl | 225 |

-continued

| Ex. No. | R¹ | R² | Acid addition salt with | Melting point/°C. |
|---|---|---|---|---|
| 295 | H | 2-methylphenyl-O-(2,6-dimethylphenyl) | — | 236 |
| 296 | H | 2-methylphenyl-O-(2-methyl-4-SCF₃-phenyl) | HOOC—CH₂—CH(OH)—COOH | 148 |
| 297 | H | 2-methylphenyl-O-(2-methyl-4-SCF₃-5-methylphenyl) | H₃PO₄ | 122 (decomp.) |
| 298 | H | 2-methylphenyl-O-(2-methyl-4-SCF₃-5-methylphenyl) | HOOC—COOH | 146 |
| 299 | H | 2-methylphenyl-O-(2-methyl-4-SCF₃-5-methylphenyl) | HOOC—CH=CH—COOH (trans) | 196 |
| 300 | H | 2-methylphenyl-O-(2-OiPr-phenyl) | HOOC—CH₂—CH(OH)—COOH | 236 |
| 301 | H | 2-methylphenyl-O-(2-tert.-Bu-4-Me-phenyl) | HOOC—CH₂—CH(OH)—COOH | 55 |
| 302 | H | 2-methylphenyl-O-(2-SCF₃-4-CH₃-6-CH₃-phenyl) | HCl | 109 |
| 303 | H | 2-methylphenyl-O-(2-SCF₃-4-CH₃-6-CH₃-phenyl) | — | 117 |

-continued

| Ex. No. | R¹ | R² | Acid addition salt with | Melting point/°C. |
|---|---|---|---|---|
| 304 | H | 2-methylphenyl-O-(2-SCF₃, 4-CH₃, 6-CH₃-phenyl) | HOOC—CH₂—CH(OH)—COOH | 95 |
| 305 | H | 2-methylphenyl-O-(2-SCF₃, 6-iPr-phenyl) | HCl | 98 |
| 306 | H | 2-methylphenyl-O-(2-SCF₃, 6-iPr-phenyl) | — | 105 |
| 307 | H | 2-methylphenyl-O-(2-tBu, 4-SCF₃-phenyl) | — | oil |
| 308 | H | 2-methylphenyl-O-(2-iPr-phenyl) | HOOC—CH₂—CH(OH)—COOH | oil |
| 309 | H | 2-methylphenyl-O-(2-SCF₃, 4-CH₃-phenyl) | HCl | 201 |
| 310 | H | 2-methylphenyl-O-(2-SCF₃, 4-CH₃-phenyl) | | 208 |
| 311 | H | 2-methylphenyl-O-(2-CH₃, 3-CH₃, 5-CH₃-phenyl) | — | 149 |
| 312 | H | 2-methylphenyl-O-(4-CH₃, 3-C(CH₃)₃-phenyl) | H₃PO₄ | 229 |

-continued

| Ex. No. | R¹ | R² | Acid addition salt with | Melting point/°C. |
|---|---|---|---|---|
| 313 | H | 2-methyl-phenoxy-4-methyl-2-tert-butyl-phenyl | COOH<br>\|<br>COOH | 198 |
| 314 | H | 2-methyl-phenoxy-4-methyl-2-tert-butyl-phenyl | CH₂—COOH<br>\|<br>CH₂—COOH | 97 |
| 315 | H | 2-methyl-phenoxy-4-methyl-2-tert-butyl-phenyl | HOOC<br>  \\<br>   CH<br>   \|\|<br>   CH<br>     \\<br>      COOH<br>(trans) | 192 |
| 316 | H | 2-SCF₃, 4-CH₃-phenoxy-2-methylphenyl | H₃PO₄ | 132 |
| 317 | H | 2-methyl-phenoxy-2-tert-butyl-phenyl | H₃PO₄ | 220 |
| 318 | H | 2-methyl-phenoxy-4-methyl-2-methyl-phenyl | COOH<br>\|<br>CH₂<br>\|<br>CHOH<br>\|<br>COOH | 126 |
| 319 | H | 2-methyl-phenoxy-4-methyl-2-methyl-phenyl | HOOC<br>  \\<br>   CH<br>   \|\|<br>   CH<br>     \\<br>      COOH<br>(trans) | 175 |
| 320 | H | 2-methyl-phenoxy-4-COOCH₃-phenyl | — | 125 |
| 321 | H | 2-methyl-phenoxy-4-COOEt-phenyl | — | 173 |

-continued

| Ex. No. | R¹ | R² | Acid addition salt with | Melting point/°C. |
|---|---|---|---|---|
| 322 | H | 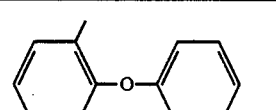 | HCl | 199–200 |
| 323 | H | 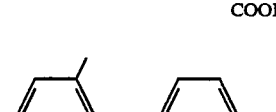 | — | 193 |

EXAMPLE 324

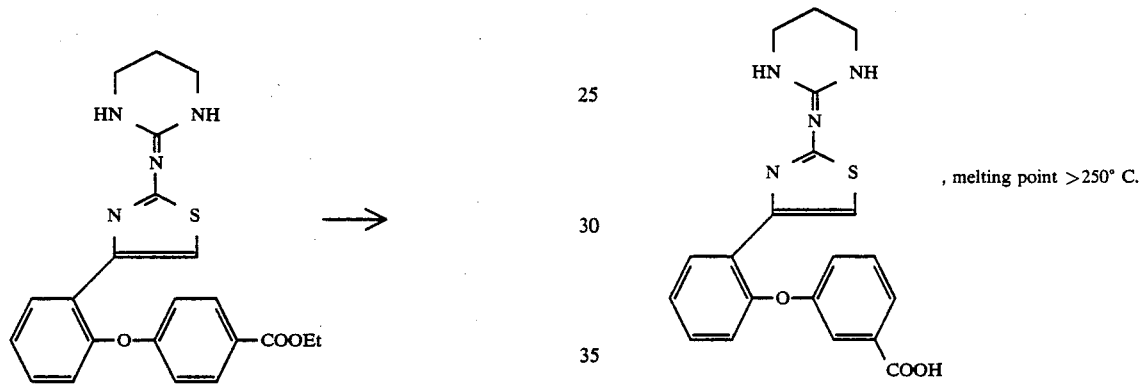

A solution of 3.45 g of KOH in 40 ml of EtOH is added dropwise to 6.3 g (0.0155 mol) of the carboxylic acid ester of Example 321, suspended in 150 ml of EtOH. The mixture is subsequently stirred at room temperature for 2 hours and then filtered off. The filtrate is concentrated by evaporation in vacuo and the residue is chromatographed on silica gel using methylene chloride/methanol 1:1 as the mobile solvent, 4.74 g (78% of theory) of the product are obtained with a melting point of higher than 250° C.

EXAMPLE 325

Following the same procedure as in Example 324 the following acid is obtained by hydrolysis of the ester of Example 323:

, melting point >250° C.

PREPARATION OF THE STARTING COMPOUNDS

EXAMPLE (III-1)

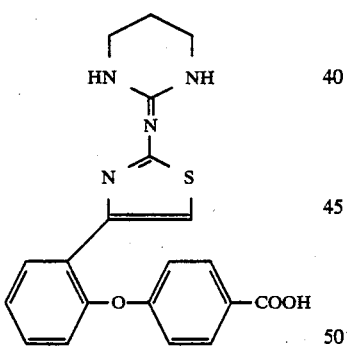

14.85 g (0.11 mol) of sulphuryl chloride are added to 24 g (0.1 mol) of 2-(2,4-dimethylphenoxy)acetophenone in 100 ml of dichloromethane, the mixture is stirred until evolution of hydrogen chloride has ended (about 2 hours) at room temperature, washed successively with 300 ml of water and 300 ml of saturated sodium hydrogencarbonate solution in each case, dried over magnesium sulphate and concentrated in vacuo.

18.9 g (69% of theory) of ω-chloro-2-(2,4-dimethylphenoxy)acetophenone are obtained as an oil which is reacted further without additional purification. ¹H-NMR$_{(CDCl_3}$/tetramethylsilane): δ=4.92 ppm.

EXAMPLE (III-2)

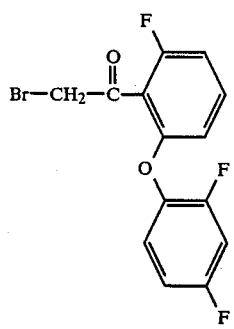

1 ml of concentrated hydrochloric acid and then, dropwise in the course of about 2 hours, 9 g (0.056 mol) of bromine in 20 ml of glacial acetic acid are added successively at room temperature with stirring to 13.3 g (0.05 mol) of 2-(2,4-difluorophenoxy)-6-fluoroacetophenone in 100 ml of glacial acetic acid. After completion of the addition, the mixture is stirred for a further 30 minutes at room temperature, then added to 450 ml of ice water and extracted several times using dichloromethane, the combined organic phases are washed with water and dried over magnesium sulphate, and the solvent is removed in vacuo.

12.2 g (70% of theory) of ω-bromo-2-(2,4-difluorophenoxy)-6-fluoroacetophenone are obtained as an oil which is reacted further without additional purification.

$^1$H-NMR (CDCl$_3$/tetramethylsilane): δ=4.51 ppm.

EXAMPLE III-3

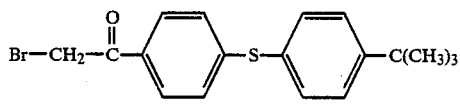

8 g (0.05 mol) of bromine in 30 ml of dichloromethane are added dropwise at room temperature with stirring to 14.2 g (0.05 mol) of 4-(4-t-butylphenylthio)acetophenone (compare, for example, U.S. Pat. No. 4,536,517) in 50 ml of dichloromethane, the reaction mixture is stirred for a further 2 hours at room temperature after completion of the addition and then poured into 400 ml of water, the mixture is extracted several times using dichloromethane, the combined organic phases are washed with saturated aqueous sodium hydrogencarbonate solution and dried over magnesium sulphate, and the solvent is removed in vacuo.

17.0 g (94% of theory) of ω-bromo-4-(4-t-butylphenylthio)acetophenone of melting point 81° C. are obtained.

The following ω-halogenoacetophenones of the formula (III)

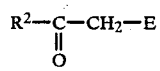

are obtained in a corresponding manner and according to the general instructions for preparation:

| Ex. No. | R$^2$ | E | $^1$H-NMR*: |
|---|---|---|---|
| III-4 | 2-methylphenoxy-2,4-difluorophenyl (F, F substituents) | Cl | 4.86 |
| III-5 | 2-methyl-6-fluorophenoxy-2-chloro-4-fluorophenyl | Cl | 4.84 |
| III-6 | 2-methylphenoxy-2-chloro-4-fluorophenyl | Cl | 4.84 |
| III-7 | 2-methylphenoxy-2-CF$_3$-4-chlorophenyl | Cl | 4.79 |
| III-8 | 2-methylphenoxy-2-CF$_3$-phenyl | Cl | 4.81 |
| III-9 | 2-methylphenoxy-2-C$_2$H$_5$-phenyl | Cl | 4.89 |
| III-10 | 2-methylphenoxy-naphthyl | Cl | 4.98 |
| III-11 | 2-methylphenoxy-2-CH(CH$_3$)$_2$-phenyl | Cl | 4.79 |
| III-12 | 2-methylphenoxy-2-Cl-4-OCF$_3$-phenyl | Cl | 4.76 |
| III-13 | 2-methylphenoxy-2-OCH$_3$-phenyl | Cl | 4.80 |
| III-14 | 2-methylphenoxy-4-OCF$_3$-phenyl | Cl | 4.79 |
| III-15 | 2-methylphenoxy-2-OCF$_3$-phenyl | Cl | 4.77 |
| III-16 | 2-methylphenoxy-2-Cl-4-SCF$_3$-phenyl | Cl | 4.75 |
| III-17 | 2-methylphenoxy-2-CH$_3$-4-SCF$_3$-phenyl | Cl | 4.78 |
| III-18 | 2-methylphenoxy-2-C(CH$_3$)$_3$-4-CH$_3$-phenyl | Cl | 4.82 |

-continued
| Ex. No. | R² | E | ¹H-NMR*: |
|---|---|---|---|
| III-19 | 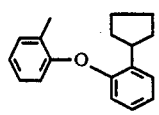 | Cl | 4.86 |
| III-20 | 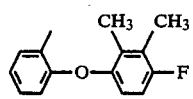 | Cl | 4.83 |
| III-21 | 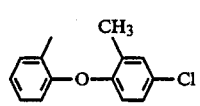 | Cl | 4.81 |
| III-22 | 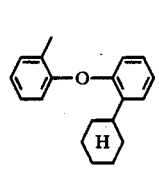 | Cl | 4.84 |
| III-23 | 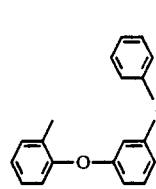 | Cl | 4.91 |
| III-24 | 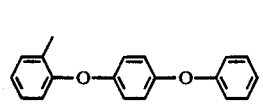 | Cl | 4.86 |
| III-25 | 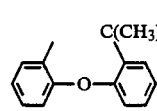 | Cl | 4.79 |
| III-26 | 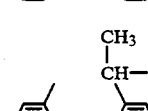 | Cl | 4.88 |
| III-27 | 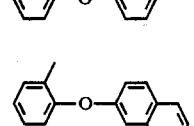 | Cl | 4.97 |
| III-28 |  | Cl | 4.84 |
| III-29 | 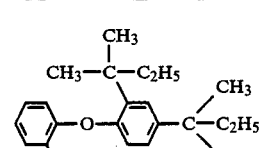 | Cl | 4.81 |
| III-30 | 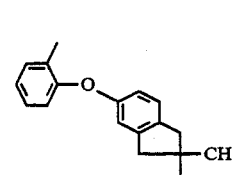 | Cl | 4.87 |
| III-31 | 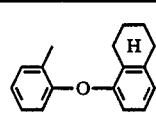 | Cl | 4.85 |
| III-32 | 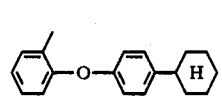 | Cl | 4.79 |
| III-33 | 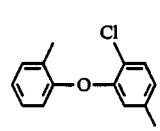 | Cl | 4.82 |
| III-34 |  | Cl | 4.85 |
| III-35 | 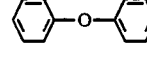 | Cl | 4.81 |
| III-36 | 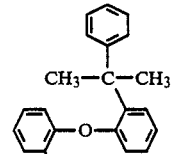 | Cl | 4.85 |
| III-37 | 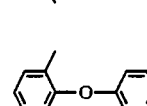 | Cl | 4.90 |
| III-38 | 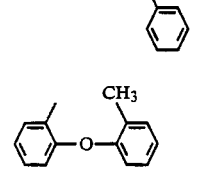 | Cl | 4.84 |
| III-39 | 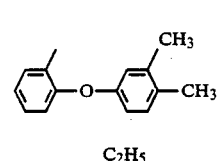 | Cl | 4.88 |
| III-40 | 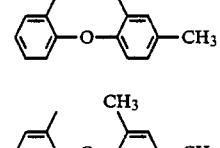 | Cl | 4.90 |
| III-41 | 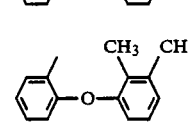 | Cl | 4.90 |
| III-42 | 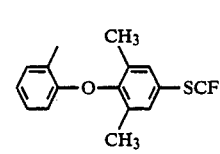 | Cl | 4.95 |

-continued

| Ex. No. | R² | E | ¹H-NMR*: |
|---|---|---|---|
| III-43 | 2-methylphenoxy-(2,3-dimethyl-4-SCF₃)phenyl | Cl | 4.81 |
| III-44 | 2-methylphenoxy-(3,5-dimethyl-4-SCF₃)phenyl | Cl | 4.75 |
| III-45 | 2-methylphenoxy-(3-OCH₃-4-SCF₃)phenyl | Cl | 4.91 |
| III-46 | 2-methylphenoxy-(3-CH₃-4-OCF₃)phenyl | Cl | 4.82 |
| III-47 | 2-methylphenoxy-(3-C₂H₅-4-SCF₃)phenyl | Cl | 4.79 |
| III-48 | 2-methylphenoxy-(3-CH₃-4-SCF₃)phenyl | Cl | 4.78 |
| III-49 | 2-methylphenoxy-(3-CH₃-5-Cl-4-SCF₃)phenyl | Cl | 4.72 |
| III-50 | 2-methylphenoxy-(3-CH(CH₃)₂-4-SCF₃)phenyl | Cl | 4.80 |
| III-51 | 2-methylphenoxy-(3-CH₃-2-Cl-4-SCF₃)phenyl | Cl | 4.75 |
| III-52 | 2-methylphenoxy-(3,5-dimethyl-4-SCF₃)phenyl | Cl | 4.81 |
| III-53 | 2-methylphenoxy-(3-Cl-5-CH₃-4-SCF₃)phenyl | Cl | 4.76 |
| III-54 | 2-methylphenoxy-(3-CH₃-4-OCF₂CHClF)phenyl | Cl | 4.78 |
| III-55 | 3-methylphenoxy-(4-Cl)phenyl | Br | 4.73 |
| III-56 | 4-methylphenoxy-(2,6-dichloro-4-NO₂)phenyl | Br | m.p. 131–132° C. |
| III-57 | 4-methylphenoxy-(2,4-dichloro)phenyl | Br | 4.68 |
| III-58 | 2-methylphenoxy-(2,4-dichloro)phenyl | Br | 4.79 |
| III-59 | 2-methylphenoxy-(2,4-dimethyl)phenyl | Br | 4.85 |
| III-60 | 3-methylphenoxy-(2,4-dimethyl)phenyl | Br | 4.82 |
| III-61 | 4-methylphenoxy-(2,4-dimethyl)phenyl | Br | 4.80 |
| III-62 | 4-methylphenoxy-(2-CH₃-4-Cl)phenyl | Br | 4.82 |
| III-63 | (3-methyl-4-(4-methylphenoxy)-nitrophenyl) | Br | 4.79 |
| III-64 | 4-methylphenoxy-4-methylphenyl | Br | 4.82 |
| III-65 | 2-methylphenoxy-(4-Cl)phenyl | Br | 4.79 |
| III-66 | 4-methylphenoxy-(4-C(CH₃)₃)phenyl | Br | 4.81 |
| III-67 | 4-methylphenoxy-(2-Cl)phenyl | Br | 4.79 |
| III-68 | 4-methylphenoxy-(2-CH₃-4-Cl)phenyl | Br | 4.81 |
| III-69 | 4-methylphenoxy-2-methylphenyl | Br | 4.83 |
| III-70 | 4-methylphenoxy-(2-CH₃-4-Cl)phenyl | Br | 4.85 |

| Ex. No. | R² | E | ¹H-NMR*: |
|---|---|---|---|
| III-71 | 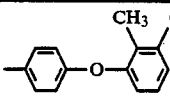 (2-methyl-3-chloro-phenoxy-phenyl) | Br | 4.81 |
| III-72 | 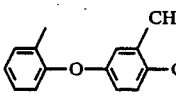 | Br | 4.83 |
| III-73 | 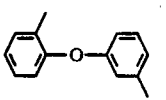 | Br | 4.79 |
| III-74 | 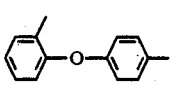 | Br | 4.82 |
| III-75 | 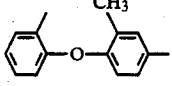 | Br | 4.81 |
| III-76 | 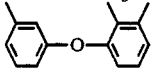 | Br | 4.83 |
| III-77 | 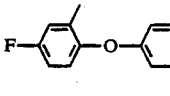 | Br | m.p. 77–78° C. |
| III-78 | 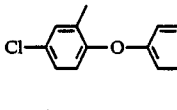 | Br | 4.77 |
| III-79 | 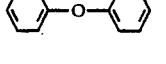 | Br | 4.88 |
| III-80 | 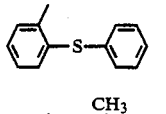 | Br | m.p. 58° C. |
| III-81 | 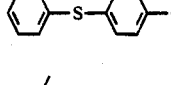 | Br | m.p. 85–86° C. |
| III-82 | 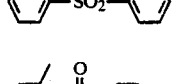 | Br | 4.58 |
| III-83 | 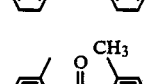 | Br | 4.50 |
| III-84 | 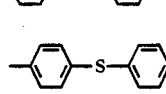 | Br | 4.61 |
| III-85 | 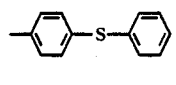 | Br | m.p. 80° C. |
| III-86 |  | Br | 4.60 |
| III-87 | 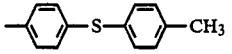 | Br | 4.61 |
| III-88 | 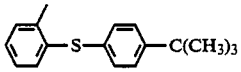 | Br | 4.64 |
| III-89 | 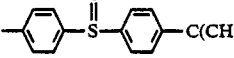 | Br | m.p. 150° C. |
| III-90 | 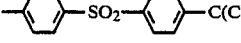 | Br | m.p. 162° C. |
| III-91 | 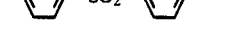 | Br | m.p. 118–119° C. |
| III-92 | 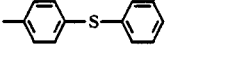 | Br | 4.62 |
| III-93 | 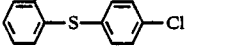 | Br | m.p. 89° C. |
| III-94 | 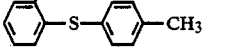 | Br | m.p. 88–89° C. |
| III-95 | 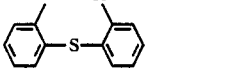 | Br | 4.61 |
| III-96 | 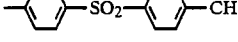 | Br | m.p. 120° C. |
| III-97 | 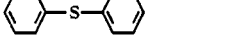 | Br | 4.60 |
| III-98 | 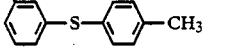 | Br | 4.59 |
| III-99 | 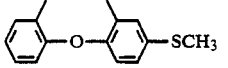 | Cl | 4.89 |
| III-100 | 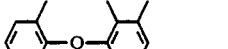 | Cl | 4.88 |
| III-101 | 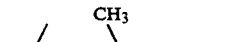 | Cl | m.p. 117–118° C. |

-continued

| Ex. No. | R² | E | ¹H-NMR*: |
|---|---|---|---|
| III-102 | (structure: phenyl-O-phenyl with SCF₃ and tButyl) | Cl | 4.87 |
| III-103 | (structure: phenyl-O-phenyl with SCF₃ and iPropyl) | Cl | 4.81 |
| III-104 | (structure: phenyl-O-phenyl with SCF₃ and Me) | Cl | 4.83 |
| III-105 | (structure: phenyl-O-phenyl with SCF₃, Me, Me) | Cl | 4.87 |
| III-106 | (structure: phenyl-O-phenyl with CH₃ and SO—CF₃) | Br | 4.58 |
| III-107 | (structure: phenyl-O-phenyl with CH₃ and SO₂CF₃) | Br | 4.59 |
| III-108 | (structure: phenyl-O-phenyl with O-iPropyl) | Cl | 4.86 |
| III-109 | (structure: phenyl-O-phenyl with iPropyl and Me) | Cl | 4.89 |
| III-110 | (structure: phenyl-O-phenyl with CH₃, CH₃) | Cl | 4.90 |
| III-111 | (structure: phenyl-O-phenyl with CH₃, CH₃) | Cl | 4.91 |
| III-112 | (structure: phenyl-O-phenyl-COOMe) | Cl | m.p. 126–127° C. |
| III-113 | (structure: phenyl-O-phenyl-COOEt) | Cl | 4.88 |

*The ¹H-NMR spectra were recorded in deuterochloroform (CDCl₃) using tetramethylsilane (TMS) as the internal standard. The chemical shift of the —CH₂—E protons is indicated as the δ value in ppm.

EXAMPLE IB-1

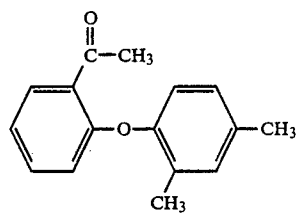

13.8 g (0.25 mol) of finely powdered potassium hydroxide are added to 36.6 g (0.3 mol) of 2,4-dimethylphenol (compare, for example, U.S. Pat. No. 3,280,200) in 100 ml of dioxane, the mixture is heated at reflux temperature for one hour, 0.5 g of finely divided copper powder and 30 g (0.15 mol) of 2-bromoacetophenone (compare, for example, J. Org. Chem. 46, 2169-2171 [1981]) are then added successively at 90°, the reaction mixture is heated to reflux temperature for a further 8 hours, allowed to cool and then added to 300 ml of water, the mixture is extracted several times using dichloromethane, the extract is dried over magnesium sulphate and concentrated in vacuo, and the residue is distilled in a high vacuum.

24.2 g (67.5% of theory) of 2-(2,4-dimethylphenoxy)acetophenone of boiling point 140°-143° C. at 0.2 mbar are obtained.

EXAMPLE IV-2

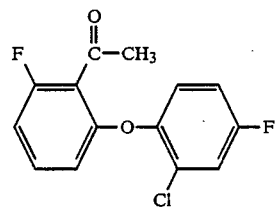

A solution of 69.2 g (0.262 mol) of 2-(2-chloro-4-fluorophenoxy)-6-fluorobenzonitrile (preparation analogous to U.S. Pat. No. 3,950,379 or J. Med. Chem. 29, 427–433 [1986]) in 500 ml of ether is added dropwise at room temperature with stirring in the course of about 30 minutes to a Grignard solution [prepared in a customary manner from 8.4 g of magnesium turnings, 35 g (0.37 mol) of bromomethane, 0.1 g of copper(I) chloride and 85 ml of ether], the reaction mixture is stirred for a further 5 hours at room temperature after completion of the addition, then added to 1700 ml of ice water, 20% strength sulphuric acid is added dropwise with stirring at 0° C. to 3° C. until the pH is 2 (about 100 ml), the mixture is stirred at room temperature for 10 minutes and the organic phase is then separated off. [Customary working up of the organic phase yields 33 g of unreacted starting material]. The aqueous phase is allowed to stand for 48 hours at room temperature and is extracted using dichloromethane, and the extract is dried over magnesium sulphate and concentrated in vacuo. The remaining oil crystallizes when allowed to stand.

22.6 g (59% of theory) of 2-(2-chloro-4-fluorophenoxy)-6-fluoroacetophenone of melting point 53° C.–54° C. are obtained.

EXAMPLE IV-3

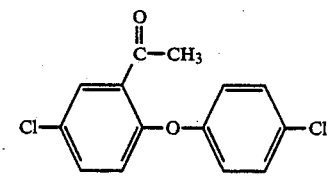

A solution of 27.6 g (0.4 mol) of sodium nitrite in 31.7 ml of water is added dropwise with stirring at 0° C. to 5° C. to 84.3 g (0.3 mol) of 5-chloro-2-(4-chlorophenoxy)aniline (compare, for example, EP No. 34,771), 284 ml of water and 72.2 ml of concentrated hydrochloric acid, the mixture is stirred for a further 15 minutes after completion of the addition and filtered, 16.4 g (0.2 mol) of sodium acetate are added to the filtrate and the solution thus obtainable is added dropwise with stirring at 10° C. to 15° C. to a mixture of 253 ml of water, 123 g (1.5 mol) of sodium acetate, 2.5 g (0.015 mol) of sodium sulphate, 15.9 g (0.1 mol) of copper(II) sulphate and 28.3 g (0.48 mol) of acetaldoxime. After completion of the addition, the mixture is stirred for one hour at room temperature, the pH is then adjusted to 7 by addition of about 40 ml of concentrated hydrochloric acid, 292 ml of concentrated hydrochloric acid are then added in portions and the mixture is heated to reflux temperature for 3 hours. The reaction mixture is subjected to a steam distillation, the oil which separates is taken up in dichloromethane, and the solution is dried over sodium sulphate, concentrated and distilled in a high vacuum.

29.5 g (35% of theory) of 5-chloro-2-(4-chlorophenoxy)acetophenone of boiling point 80°–85° C. at 1.5 mbar are obtained.

EXAMPLE IV-4

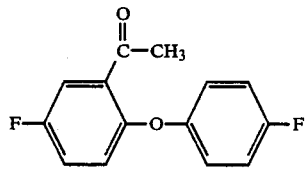

First 7.21 g (0.035 mol) of 4,4,-difluorodiphenyl ether (compare, for example, Synth. Commun. 17, 685–692 [1987]) and then, in portions, 6.05 g (0.0455 mol) of aluminum trichloride are added dropwise with stirring to 3.02 g (0.0385 mol) of acetyl chloride in 250 ml of dichloromethane, the reaction mixture is then stirred at room temperature for 5 hours and poured into ice water, the mixture is extracted using dichloromethane, the extract is dried over sodium sulphate and concentrated in vacuo, and the residue is chromatographed on silica gel (eluent: dichloromethane).

2.2 g (25.3% of theory) of 5-fluoro-2-(4-fluorophenoxy)acetophenone are obtained as the 2nd fraction; $^1$H-NMR (CDCl$_3$): δ =2.63 ppm and 0.8 g (9.2% of theory) of 2-fluoro-5-(4-fluorophenoxy)acetophenone; $^1$H-NMR (CDCl$_3$):δ =2.61 ppm as the 3rd fraction.

EXAMPLE IV-5

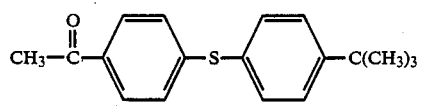

13.19 g (0.079 mol) of 4-t-butylthiophenol are added to 4.2 g (0.075 mol) of potassium hydroxide in 125 ml of dimethylformamide, the mixture is stirred for 1 hour at room temperature, 12.4 g (0.062 mol) of 4-bromoacetophenone are then added and the mixture is heated to reflux temperature for 16 hours. For working up, the cooled reaction mixture is poured into 200 ml of water, the mixture is extracted several times using dichloromethane, the combined organic phases are washed with water, dried over magnesium sulphate and concentrated in vacuo, and the residue is distilled in a high vacuum.

14.3 g (81% of theory) of 4-(4-t-butylphenylthio)acetophenone of boiling point 173°-175° C. at 0.3 mbar and melting point 50° C. are obtained.

EXAMPLE IV-6

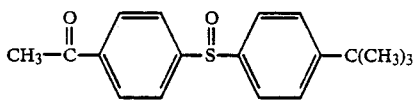

8.9 g (0.04 mol) of m-chloroperbenzoic acid (80% strength) dissolved in 100 ml of dichloromethane are added dropwise with stirring at 25° C. to 30° C. to 10.4 g (0.035 mol) of 4-(4-t-butylphenylthio)acetophenone in 100 ml of absolute dichloromethane, the mixture is stirred at room temperature for a further 20 hours after completion of the addition, the precipitate is filtered off with suction, the filtrate is washed successively twice with saturated aqueous sodium hydroirogencarbonate solution and then with saturated aqueous sodium chloride solution, dried over magnesium sulphate and concentrated in vacuo, and the residue is recrystallized from ethanol.

6.93 g (63% of theory) of 4-(4-t-butylphenylsulphinyl)acetophenone of melting point 148° C. are obtained.

EXAMPLE IV-7

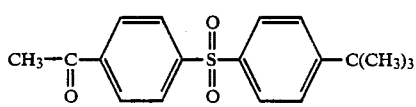

18.38 g (0.08 mol) of m-chloroperbenzoic acid (80% strength) dissolved in 200 ml of dichloromethane are added dropwise with stirring at 25° C. to 30° C. to 10.4 g (0.035 mol) of 4-(4-t-butylphenylthio)acetophenone in 100 ml of absolute dichloromethane, the mixture is stirred for a further 20 hours at room temperature after completion of the addition, the precipitate is filtered off with suction, the filtrate is washed successively twice with saturated aqueous sodium hydrogencarbonate solution and then with saturated aqueous sodium chloride solution, dried over magnesium sulphate and concentrated in vacuo, and the residue is recrystallized from ethanol.

6.7 g (58% of theory) of 4-(4-t-butylphenylsulphonyl-)acetophenone of melting point 155° C. are obtained.

The following acetophenones of the general formula (IV)

are obtained in a corresponding manner and according to the general instructions for preparation:

| Ex. No. | R² | Physical properties |
|---|---|---|
| IV-8 | 2-methylphenoxy-(4-chloro-2-trifluoromethyl)phenyl | b.p. 125–126° C./ 0.2 mbar |
| IV-9 | 2-methylphenoxy-(3-trifluoromethyl)phenyl | b.p. 106–108° C. 0.3 mbar |
| IV-10 | 2-methylphenoxy-(2-ethyl)phenyl | b.p. 126–128° C./ 0.2 mbar |
| IV-11 | 2-methylphenoxy-(2-methoxy)phenyl | b.p. 130–132° C./ 0.2 mbar |
| IV-12 | 2-methylphenoxy-(1-naphthyl) | b.p. 156–160° C./ 0.2 mbar |
| IV-13 | 2-methylphenoxy-(2-cyclohexyl)phenyl | b.p. 156–158° C./ 0.2 mbar |
| IV-14 | 2-methylphenoxy-(2-isopropyl)phenyl | b.p. 136–138° C./ 0.2 mbar |
| IV-15 | 2-methylphenoxy-(2-t-butyl-4-methyl)phenyl | b.p. 150–152° C./ 0.2 mbar |

-continued
| Ex. No. | R² | Physical properties |
|---|---|---|
| IV-16 | 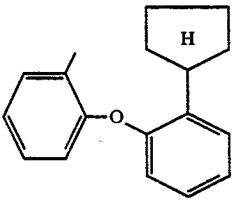 | b.p. 157–160° C./ 0.1 mbar |
| IV-17 | 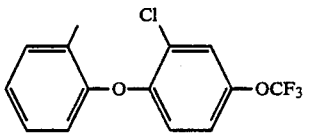 | b.p. 128° C./ 0.2 mbar |
| IV-18 | 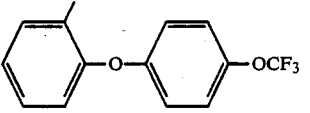 | b.p. 123–125° C./ 0.2 mbar |
| IV-19 | 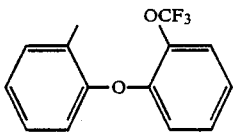 | b.p. 108–110° C./ 0.2 mbar |
| IV-20 | 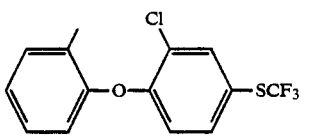 | b.p. 140–142° C./ 0.2 mbar |
| IV-21 | 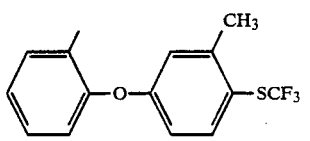 | b.p. 135–138° C./ 0.2 mbar |
| IV-22 | 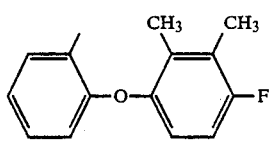 | b.p. 137° C./ 0.1 mbar |
| IV-23 | 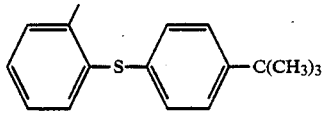 | m.p. 170° C. |
| IV-24 | 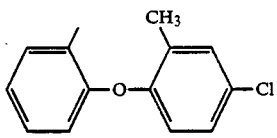 | b.p. 150–152° C./ 0.8 mbar |
| IV-25 | 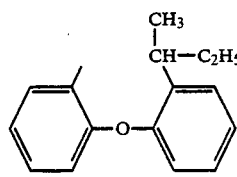 | b.p. 132–135° C./ 0.3 mbar |

-continued
| Ex. No. | R² | Physical properties |
|---|---|---|
| IV-26 | 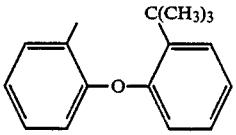 | b.p. 140–142° C./ 0.2 mbar |
| IV-27 | 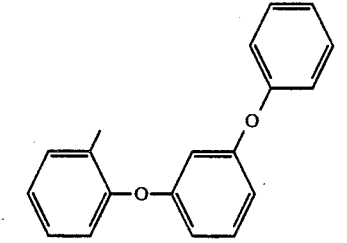 | ¹H—NMR*: 2.62 |
| IV-28 | 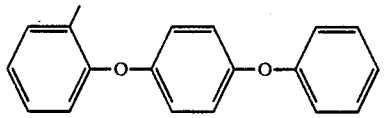 | ¹H—NMR*: 2.62 |
| IV-29 | 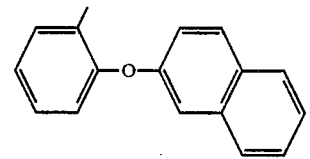 | b.p. 168–170° C./ 0.2 mbar |
| IV-30 | 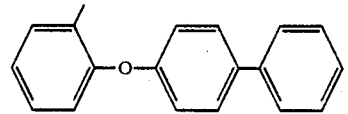 | ¹H—NMR*: 2.64 |
| IV-31 | 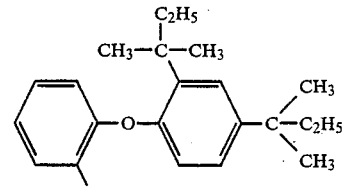 | b.p. 186–190° C./ 0.1 mbar |
| IV-32 | 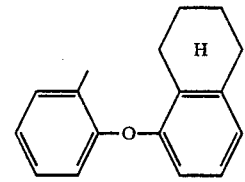 | b.p. 177–180° C./ 0.1 mbar |
| IV-33 | 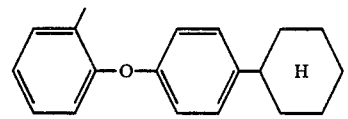 | b.p. 166–170° C./ 0.15 mbar |

-continued

| Ex. No. | R² | Physical properties |
|---|---|---|
| IV-34 | (2-methylphenoxy)-2,2-dimethylindane | b.p. 180–182° C./ 0.2 mbar |
| IV-35 | 2-(2-methylphenoxy)biphenyl | ¹H—NMR*: 2.65 |
| IV-36 | 2,2'-(2-methylphenoxy)phenyl, α,α-dimethylbenzyl | m.p. 99° C. |
| IV-37 | 2,4-dichloro-(2-methylphenoxy)benzene | b.p. 118–120° C./ 0.2 mbar |
| IV-38 | 3-(2-methylphenoxy)biphenyl | ¹H—NMR*: 2.68 |
| IV-39 | 2-methyl-(2-methylphenoxy)benzene | b.p. 135–138° C./ 0.2 mbar |
| IV-40 | 3,4-dimethyl-(2-methylphenoxy)benzene | b.p. 146–148° C./ 0.3 mbar |
| IV-41 | 2,4-dimethyl-(2-methylphenoxy)benzene | b.p. 133–135° C./ 0.2 mbar |

-continued

| Ex. No. | R² | Physical properties |
|---|---|---|
| IV-42 | 2-(o-tolyloxy)-3-ethyl-5-methylphenyl | b.p. 138-139° C./ 0.2 mbar |
| IV-43 | 2-(o-tolyloxy)-3,4-dimethylphenyl | b.p. 150-152° C./ 0.2 mbar |
| IV-44 | 4-(o-tolyloxy)-3,5-dimethyl-SCF₃-phenyl | b.p. 145-148° C./ 0.2 mbar |
| IV-45 | 4-(o-tolyloxy)-2,3-dimethyl-SCF₃-phenyl | b.p. 138-140° C./ 0.2 mbar |
| IV-46 | 4-(o-tolyloxy)-2,6-dimethyl-SCF₃-phenyl | b.p. 140-144° C./ 0.2 mbar |
| IV-47 | 4-(o-tolyloxy)-3-methoxy-SCF₃-phenyl | b.p. 147-150° C./ 0.2 mbar |
| IV-48 | 4-(o-tolyloxy)-3-ethyl-SCF₃-phenyl | b.p. 153-155° C./ 0.4 mbar |
| IV-49 | 4-(o-tolyloxy)-3-methyl-OCF₃-phenyl | b.p. 118-120° C./ 0.2 mbar |
| IV-50 | 4-(o-tolyloxy)-3-methyl-SCF₃-phenyl | b.p. 133-136° C./ 0.2 mbar |
| IV-51 | 4-(o-tolyloxy)-3-methyl-5-chloro-SCF₃-phenyl | b.p. 143-145° C./ 0.2 mbar |

-continued

| Ex. No. | R² | Physical properties |
|---|---|---|
| IV-52 | 2-methylphenyl-O-(2-isopropyl-4-SCF₃-phenyl) | b.p. 130–132° C./ 0.2 mbar |
| IV-53 | 2-methylphenyl-O-(2-CH₃-3-Cl-4-SCF₃-phenyl) | b.p. 142–144° C./ 0.2 mbar |
| IV-54 | 2-methylphenyl-O-(2-CH₃-5-CH₃-4-SCF₃-phenyl) | b.p. 143–144° C./ 0.2 mbar |
| IV-55 | 2-methylphenyl-O-(2-Cl-5-CH₃-4-SCF₃-phenyl) | ¹H—NMR*: 2.59 |
| IV-56 | 2-methylphenyl-O-(2-CH₃-4-O-CF₂-CHClF-phenyl) | b.p. 171–173° C./ 0.2 mbar |
| IV-57 | 4-methylphenyl-O-(3-CH₃-4-Cl-phenyl) | ¹H—NMR*: 2.61 |
| IV-58 | 4-methylphenyl-O-(4-Cl-phenyl) | b.p. 138–140° C./ 0.15 mbar |
| IV-59 | 2-methylphenyl-O-(4-Cl-phenyl) | b.p. 136–139° C./ 0.2 mbar |
| IV-60 | 3-methylphenyl-O-(4-Cl-phenyl) | b.p. 135–138° C./ 0.3 mbar |
| IV-61 | 4-methylphenyl-O-(2,4-dichlorophenyl) | ¹H—NMR*: 2.66 |

-continued
| Ex. No. | R² | Physical properties |
|---|---|---|
| IV-62 | 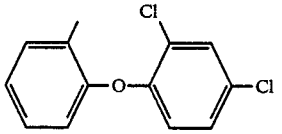 | b.p. 140° C./ 0.3 mbar |
| IV-63 | 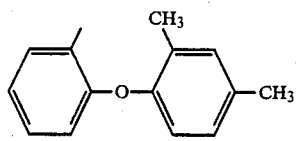 | b.p. 141–142° C./ 0.2 mbar |
| IV-64 | 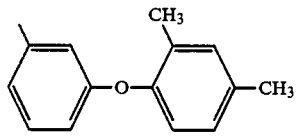 | b.p. 127–130° C./ 0.3 mbar |
| IV-65 | 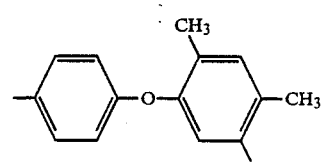 | b.p. 127–130° C./ 0.4 mbar |
| IV-66 | 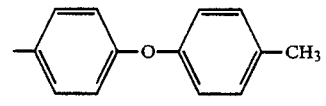 | m.p. 46–47° C. |
| IV-67 | 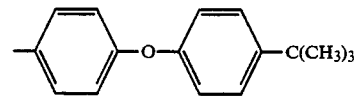 | ¹H—NMR*: 2.63 |
| IV-68 | 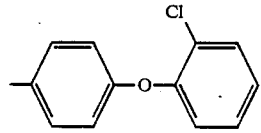 | ¹H—NMR*: 2.60 |
| IV-69 | 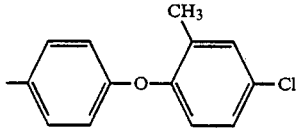 | ¹H—NMR*: 2.62 |
| IV-70 | 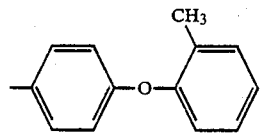 | ¹H—NMR*: 2.61 |
| IV-71 | 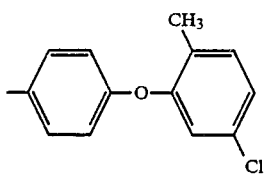 | ¹H—NMR*: 2.62 |
| IV-72 | 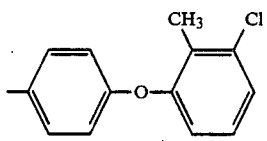 | ¹H—NMR*: 2.64 |

-continued
| Ex. No. | R² | Physical properties |
|---|---|---|
| IV-73 | 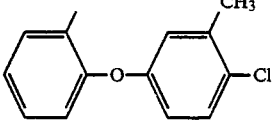 | ¹H—NMR*: 2.64 |
| IV-74 | 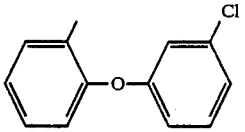 | m.p. 43–44° C. |
| IV-75 | 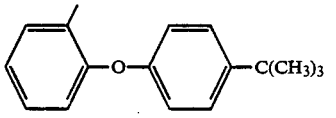 | ¹H—NMR*: 2.63 |
| IV-76 | 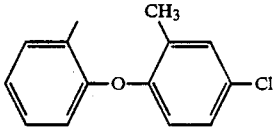 | ¹H—NMR*: 2.61 |
| IV-77 | 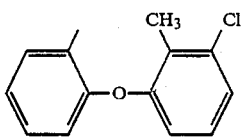 | ¹H—NMR*: 2.61 |
| IV-78 | 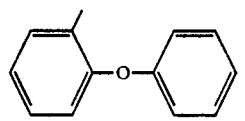 | b.p. 118–120° C./ 0.15 mbar |
| IV-79 | 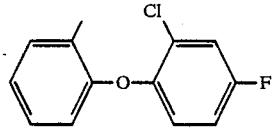 | m.p. 59–60° C. |
| IV-80 | 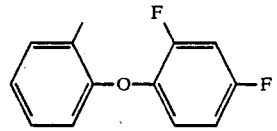 | b.p. 106–108° C./ 0.15 mbar |
| IV-81 | 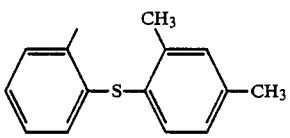 | m.p. 111° C. |
| IV-82 | 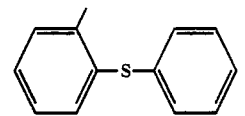 | m.p. 71–73° C. |
| IV-83 | 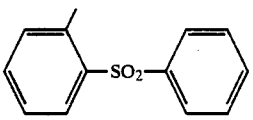 | ¹H—NMR*: 2.67 |

-continued
| Ex. No. | R² | Physical properties |
|---|---|---|
| IV-84 | 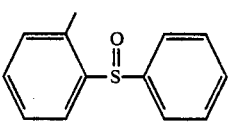 | m.p. 132–133° C. |
| IV-85 | 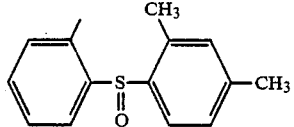 | m.p. 148° C. |
| IV-86 | 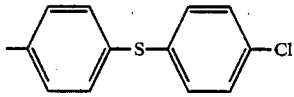 | m.p. 50° C. |
| IV-87 | 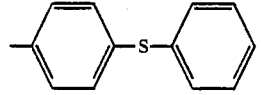 | m.p. 56–57° C. |
| IV-88 | 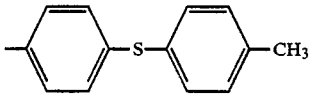 | m.p. 86° C. |
| IV-89 | 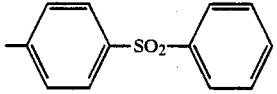 | m.p. 134–135° C. |
| IV-90 | 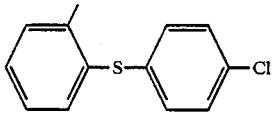 | m.p. 83° C. |
| IV-91 | 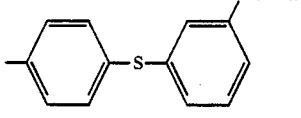 | b.p. 178–180° C./ 0.2 mbar |
| IV-92 | 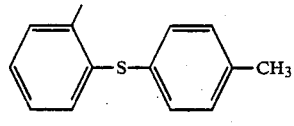 | m.p. 99° C. |
| IV-93 | 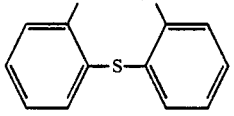 | b.p. 175° C./ 0.2 mbar |
| IV-94 | 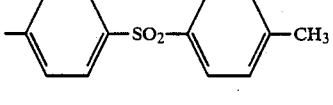 | m.p. 157° C. |
| IV-95 | 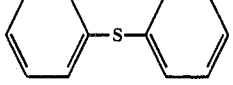 | b.p. 145° C./ 0.3 mbar |

-continued

| Ex. No. | R² | Physical properties |
|---|---|---|
| IV-96 | 3-methylphenyl-S-(4-methylphenyl) | b.p. 148–150° C./ 0.2 mbar |
| IV-97 | 2-methylphenyl-O-(2-methyl-4-SCH₃-phenyl) | b.p. 171–173° C./ 0.15 mbar |
| IV-98 | 2-methylphenyl-O-(2,3,5-trimethylphenyl) | b.p. 188–190° C./ 0.15 mbar |
| IV-99 | 2-methylphenyl-O-(2,6-dimethylphenyl) | b.p. 148–150° C./ 0.1 mbar |
| IV-100 | 2-methylphenyl-O-(3-tButyl-4-SCH₃-phenyl) | ¹H—NMR: 2.73 |
| IV-101 | 2-methylphenyl-O-(2-SCF₃-6-iPropyl-phenyl) | m.p. 120–122° C./ 0.03 mbar |
| IV-102 | 2-methylphenyl-O-(2-SCF₃-4-Me-phenyl) | b.p. 124–125° C./ 0.2 mbar |
| IV-103 | 2-methylphenyl-O-(2-SCF₃-4-Me-6-Me-phenyl) | b.p. 123–125° C./ 0.2 mbar |
| IV-104 | 2-methylphenyl-O-(2-CH₃-4-SOCF₃-phenyl) | 2.60 |
| IV-105 | 2-methylphenyl-O-(2-CH₃-4-SO₂CF₃-phenyl) | 2.58 |

-continued

| Ex. No. | R² | Physical properties |
| --- | --- | --- |
| IV-106 | [structure: 2-methylphenyl-O-(2-methyl-6-OiPropyl)phenyl ether] | b.p. 151–153° C./ 0.2 mbar |
| IV-107 | [structure: 2-methylphenyl-O-(2-iPropyl-5-Me)phenyl ether] | b.p. 157–159° C./ 0.15 mbar |
| IV-108 | [structure: 2-methylphenyl-O-phenyl-COOCH₃] | b.p. 157–160° C./ 0,2 mbar |
| IV-109 | [structure: 2-methylphenyl-O-phenyl-COOEt] | b.p. 152–155° C./ 0,2 mbar |

*The $^1$H—NMR spectra were recorded in deuterochloroform (CDCl$_3$) using tetramethylsilane (TMS) as the internal standard. The chemical shift is indicated as the δ value in ppm.

INTERMEDIATES

EXAMPLE VIIa-1

3-[(α,α,β,β-Tetrafluoroethyl)thio]phenol 126 g (1 mol) of 4-mercaptophenyl and 11.2 g (0.2 mol) of potassium hydroxide were dissolved in 300 ml of ethylformide. The apparatus gas flushed with nitrogen at an internal temperature of 90° to 100° C. and tetrafluoroethylene was then introduced with vigorous stirring. As soon as the latter was no longer absorbed, 75% by volume of the dimethylformamide was stripped off in vacuo, the residue was stirred into 500 ml of ice water, the mixture was brought to a pH of 3.5, and the organic phase was isolated and distilled. 167 g of product having a boiling point of 72° to 73° C. at 17 mbar were obtained.

EXAMPLE VIIa-2

2,3,6-Trichloro-4-trifluoromethoxyphenol 89 g (0.5 mol) of 4-trifluoromethoxyphenol were dissolved in 150 ml of carbon tetrachloride. After addition of 0.5 g of iron powder, chlorine was introduced at 40° C. The course of the reaction was checked by gas chromatography. After a content of 98% of trichloro product had been attained, the chlorine was blown out with nitrogen and the mixture was then fractionally distilled. 106 g of product having a boiling point of 120° to 122° C. at 20 mbar were obtained, which corresponds to a yield of 74% of theory. The melting point of the product was 56° to 58° C.

EXAMPLE VIIa-3

2-Nitro-4-trifluoromethoxyphenol 53.4 g (0.3 mol) of 4-trifluoromethoxyphenol were allowed to drop at 25° C. in the course of 30 minutes into 75 ml of 30% strength nitric acid. The mixture was subsequently stirred for 2 hours at 25° C. and then poured into 500 ml of ice water, and the organic phase was separated off. Distillation of the latter yielded 56 g of product having a boiling point of 102° to 103° C. at 26 mbar, which corresponds to a yield of 83% of theory.

EXAMPLE VIIa-4

2,6-Dinitro-4-trifluoromethoxyphenol 53.4 g (0.3 mol) of 4-trifluoromethoxyphenol were allowed to drop at 60° C. in the course of 1 hour into 150 ml of 40% strength nitric acid. The mixture was subsequently stirred for a further 5 hours at 60° C. and then worked up as in Example 3. 63 g of product having a boiling point of 126° to 128° C. at 0.1 mbar were obtained, which corresponds to 78% of theory.

EXAMPLE VIIa-5

2-Hydroxy-5-trifluoromethoxybenzoic acid 178 g (1 mol) of 4-trifluoromethoxyphenol and 345 g (2.5 mol) of potassium carbonate were initially introduced into an autoclave which was then pressurized to 60 bar with carbon dioxide and heated at 200° C. for 4 hours. After cooling and releasing the pressure, the residue was dissolved in 1.5 l of hot water, the solution was filtered hot, the cooled filtrate was extracted using methylene chloride and the extract was clarified using active carbon. The pH was then adjusted to 1 and the precipitated product was filtered off with suction. 192 g of product having a melting point of 129° C. were obtained, which corresponds to 86% of theory.

EXAMPLE VIIa-6

2-Hydroxy-5-trifluoromethylthiobenzoic acid

The procedure was as described in Example 5, but 194 g (1 mol) of 4-trifluoromethylmercaptophenol were employed and 185.7 g of product having a melting point of 122° to 125° C. were obtained, which corresponds to 78% of theory.

EXAMPLE VIIa-7

2-Hydroxy-5-trifluoromethoxybenzamide 100 g (0.45 mol) of 2-hydroxy-5-tifluoromethoxybenzoic acid (obtained according to Example 5) were initially introduced into 350 ml of petroleum ether. After the addition of 1 ml of pyridine, 56 g of SOCl$_2$ were allowed to drop in the course of 30 minutes at 30° C. and the mixture was subsequently stirred for a further hours at 30° C. The solution was then decanted off from an oily reaction residue and saturated with ammonia gas. The precipitated solid was filtered off and dried. 82 g of product having a melting point of 188° to 190° C. were obtained, which corresponds to 75% of theory.

EXAMPLE VIIa-8

3,4-bis-Trifluoromethoxyphenol (a) Preparation of the 3,4-bis-trifluoromethoxyaniline required as precursor 415 g (3 mol) of veratrole and 5 g of azobisisobutyronitrile were dissolved in 3 l of carbon tetrachloride and the mixture was heated to reflux temperature. 2.2 kg of chlorine were introduced under UV irradiation, which took about 30 hours, and at the same time 20 g of azobisisobutyronitril were added, distributed uniformly over the period of the reaction. After the end of the reaction, the chlorine was blown out with nitrogen, and the mixture was concentrated and fractionally distilled. 650 g of 92% strength 1,2-bistrichloromethoxybenzene having a boiling point of 106° to 108° C. at 0.2 mbar were obtained.

50 ml of hydrogen fluoride were allowed to drop at −5° to 0° C. into 375 g of the 1,2-bistrichloromethoxybenzene thus obtained, which took 5 hours, 2.5 ml of antimony pentachloride were added and the mixture was then heated at 140° C. for 12 hours. The hydrogen chloride formed was continuously released at 25 bar. After the end of the reaction, excess hydrogen fluoride was distilled off, the distillation residue was stirred into 500 ml of water and the organic phase was separated off. 178 g of 98% strength 1,2-bistrifluoromethoxybenzene were obtained by fractionation of the organic phase.

248 g of the 1,2-bistrifluoromethoxybenzene thus obtained were allowed to drop at 0° C. in the course of 2 hours into 250 g of a mixture of 33% by weight of nitric acid and 67% by weight of sulphuric acid. The mixture was subsequently stirred at 0° C. for 5 hours, then added to ice water, and the organic phase was separated off and distilled. 284 g of 99% strength 3,4-bistrifluoromethoxynitrobenzene were obtained.

291 g of the 3,4-bistrifluoromethoxynitrobenzene thus obtained were hydrogenated with 20 bar of hydrogen in the course of 3 hours at 40° C. in 500 ml of methanol with the addition of 10 g of Raney nickel. After filtering off the catalyst with suction, the filtrate was fractionally distilled and 242 g of 3,4-bistrifluoromethoxyaniline were obtained.

(b) Preparation of 3,4-bistrifluoromethoxyphenol 356 g (1.36 mol) of 3,4-bistrifluoromethoxyaniline were diazotized in 625 g of water and 332 g of concentrated hydrochloric acid using 246 g of 40% strength sodium nitrite solution. The diazonium salt solution was allowed to drop into a hot mixture of 520 g of water, 968 g of concentrated sulphuric acid and 1200 g of xylene at 120° C. so that an internal temperature of 120° C. was able to be maintained there by azeotropic distillation of the water. The xylene phase was then separated off and the 3,4-bistrifluoromethoxyphenol formed was isolated by extraction with alkali solution. 200 g of product having a boiling point of 86° to 88° C. at 25 mbar were obtained by distillation, which corresponds to 53% of theory.

EXAMPLE VIIa-9

3-($\alpha,\alpha,\beta,\beta$-Tetrafluoroethoxy)-4-methylphenol (a) Preparation of the 3-($\alpha,\alpha,\beta,\beta$-tetrafluoroethoxy)-4-methylaniline required as precursor 165 g of 3-hydroxy-4-methylacetanilide and 25 g of potassium hydroxide were heated to 95° C. in 850 g of dimethylformamide. 120 g of tetrafluoroethylene were introduced in the course of 5 hours with vigorous stirring. After aqueous working up, 114 g of 3-($\alpha,\alpha,\beta,\beta$-tetrafluoroethoxy)-4-methylacetanilide were obtained. 375 ml of 25% strength sodium hydroxide solution were added to 265 g of the 3-($\alpha,\alpha,\beta,\beta$-tetrafluoroethoxy)-4-methylacetanilide thus prepared in 1.25 l of methanol and the mixture was heated at 70° C. for 12 hours. After the mixture had been concentrated to about 50% of the original volume, it was worked up with water. Distillation of the organic phase yielded 192 g of 3-($\alpha,\alpha,\beta,\beta$-tetrafluoroethoxy)-4-methoxyaniline.

(b) Preparation of 3-($\alpha,\alpha,\beta,\beta$-tetrafluoroethoxy)-4-methylphenol 224 g of 3-($\alpha,\alpha,\beta,\beta$-tetrafluoroethoxy)-4-methylaniline were reacted analogously to Example 8. 153.5 g of product having a boiling point of 78° to 79° C. at 0.25 mbar were obtained, which corresponds to 68% of theory.

EXAMPLE VIIa-10

2-Methyl-4-trifluoromethoxyphenol 191 g (1 mol) of 2-methyl-4-trifluoromethoxyaniline were reacted analogously to Example 8. 156 g of product having a melting point of 72° C. and a boiling point of 80° C. to 180° C. at 12 mbar were obtained, which corresponds to 81% of theory.

EXAMPLE VIIa-11

2-Methyl-4-($\alpha,\alpha,\beta$-trifluoro-$\beta$-chloroethoxy)phenol 238.5 g (1 mol) of 2-methyl-4-($\alpha,\alpha,\beta$-trifluoro-$\beta$-chloroethoxy)aniline were reacted analogously to Example 8. 192.5 g of product having a boiling point of 83° to 84° C. at 0.35 mbar were obtained, which corresponds to 80% of theory.

EXAMPLE VIId-1 to VIId-12

General working procedure 1.64 mol of phenol of the formula (VIIe) were initially introduced into 800 ml of di-tert.-butyl ether, 1.8 mol of pyridine were added and 1.65 to 1.70 mol of trifluoromethylsulphenyl chloride were introduced at 20° C. The mixture was then heated at 50° C. for 4 hours with stirring. Nitrogen was then blown through the reaction mixture (gas discharge via a washer filled with aqueous ammonia). Pyridine hydrochloride was then separated off by filtration, readily volatile constituents (essentially di-tert.-butyl ether) were distilled off under reduced pressure and crude 4-trifluoromethylmercaptophenol was thus obtained. Purification was carried out by precision distillation or by chromatography, chromatographic purification being carried out as follows:

A column (internal diameter 45 mm) was packed with a suspension of silica gel in toluene to a height of 40 cm. The crude 4-trifluoromethylmercaptophenol was dissolved in a little toluene and introduced into the column. It was then chromatographed using toluene. The toluene was distilled off under reduced pressure from the respective 2nd fraction and the 4-trifluoromercaptophenols were thus obtained in pure form.

EXAMPLE VIId-13

4-Trifluoromethylmercapto-2,3-dimethylphenol by TiCl₄ catalysis 100 g of 2,3-dimethylphenol were initially introduced into 500 ml of dichloromethane and 10 ml of titanium tetrachloride were added. 50 g of trifluoromethylsulphenyl chloride were then introduced at 20° C. and the mixture was subsequently stirred for 3 hours. 100 ml of water were then stirred in, the phases were separated and the organic phase was distilled. After a forerun, consisting of dimethylphenol and product, 68 g of product distilled at 85°–88° C./6 mbar.

EXAMPLES VIId-14 to VIId-17

General working procedure 0.08 mol of a 4-trifluoromethylmercaptophenol of the formula (VIId) was initially introduced into 80 ml of acetic acid, 35 g of 35% strength hydrogen peroxide were added dropwise and the mixture was heated at 90° C. for 3 hours. After cooling, the mixture was stirred into 200 ml of water and the precipitated product was filtered.

The examples carried out individually are summarized in the following table.

TABLE

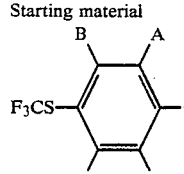

| Example No. | Starting material (A, B, C, D) | Melting point [°C.] | Yield [% of theory] |
|---|---|---|---|
| VIId-14 | A = OCH₃; B = C = D = hydrogen | 121 | 83 |
| VIId-15 | A = CH₃; C = Cl; B = D = hydrogen | 111 | 91 |
| VIId-16 | A = B = CH₃; C = D = hydrogen | 83 | 74 |
| VIId-17 | A = D = CH₃; B = C = hydrogen | 151 | 94 |

The examples carried out individually are summarized in the following table.

TABLE

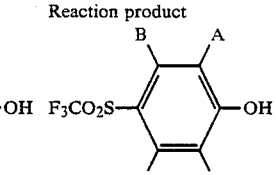

| | | Physical data of the purified reaction product | | |
|---|---|---|---|---|
| Example No. | Starting material (A, B, C, D) | b.p. °C./mbar | $n_D^{20}$ | m.p. °C. |
| VIId-1 | A = C₂H₅; B = C = D = hydrogen | 97–98/10 | 1.5030 | n.d. |
| VIId-2 | A = CH(CH₃)₂; B = C = D = hydrogen | 92–94/10 | 1.4955 | n.d. |
| VIId-3 | A = OCH₃; B = C = D = hydrogen | 94–96/12 | 1.5070 | n.d. |
| VIId-4 | A = D = CH₃; B = C = hydrogen | 122–124/22 | n.d. | 38–40 |
| VIId-5 | A = B = CH₃; C = D = hydrogen | 120–123/16 | 1.5174 | n.d. |
| VIId-6 | B = C = CH₃; A = D = hydrogen | 127–130/16 | n.d. | 68 |
| VIId-7 | A = CH₃; B = Cl; C = D = hydrogen | 125–128/16 | n.d. | 48–50* |
| VIId-8 | A = CH₃; C = Cl; B = D = hydrogen | 107–108/10 | 1.5280 | n.d.* |
| VIId-9 | A = C = CH₃; B = D = hydrogen | 104–106/10 | 1.5090 | n.d. |
| VIId-10 | A = Cl; C=CH₃; B = D = hydrogen | 125/14 | 1.5380 | n.d. |
| VIId-11 | A = C(CH₃)₃; B = C = D = hydrogen | 110–112/10 | 1.4945 | n.d. |
| VIId-12 | A = C = D = hydrogen; B = F | 72–73/10 | 1.5045 | n.d. |

*In these examples the product was purified by chromatography, otherwise the products were purified by precision distillation.
n.d. not determined

USE EXAMPLES

The compounds shown below were employed as comparison substances in the following use examples:

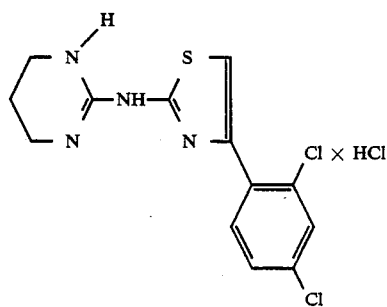

4-(2,4-dichlorophenyl)-2-[2-(1,4,5,6-tetrahydropyrimidinyl)amino]thiazole hydrochloride

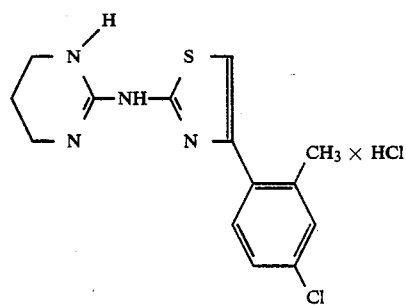

4-(4-chloro-2-methylphenyl)-2-[2-(1,4,5,6-tetrahydropyrimidinyl)amino]thiazole hydrochloride

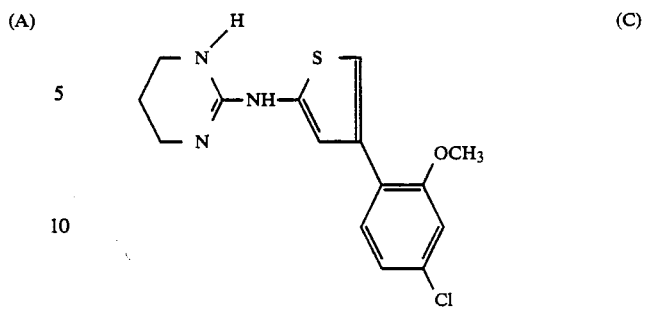

4-(4-chloro-2-methoxyphenyl)-2-[2-(1,4,5,6-tetrahydropyrimidinyl)amino]thiazole (all known from German Offenlegungsschrift No. 3,220,118)

EXAMPLE A

Antimycotic in vitro activity

Description of experiment:

The in vitro tests were carried out using inocula of microorganisms of on average $5 \times 10^3$ microorganisms/ml of substrate. Yeast nitrogen base medium was used as a nutrient medium for yeasts and kimmig medium for hyphomycetes.

The incubation temperature was 37° C. with yeasts and 28° C. with hyphomycetes, and the incubation period was 24 to 96 hours with yeasts and 96 to 120 hours with hyphomycetes.

The evaluation of the fungicides was carried out by plating out and incubating completely inhibited batches again. Fungicidal concentrations contained less than 100 microorganisms CFU (colony forming unit) per ml.

In this test, the compounds, according to the invention, of the formula (I) according to Preparation Examples 3, 6, 16, 25, 30, 35, 42, 45, 47, 48, 50, 92, 98, 116, 132, 133, 134, 135, 137, 147, 149, 150, 151, 153 and 181 show a clearly better antimycotic activity than the comparison compounds (A), (B) and (C) known from the prior art.

TABLE A

| Active compound | Antimycotic in vitro activity MFC* values in μg/ml of nutrient medium | | | |
|---|---|---|---|---|
| | Trichophython mentagrophytes | Aspergillus fumigatus | Candida albicans | Torulopsis glabrata |
| (A) (known) | 16 | 64 | 16 | 32 |
| (B) (known) | 16 | 64 | 64 | >64 |

TABLE A-continued
Antimycotic in vitro activity
MFC* values in μg/ml of nutrient medium
| Active compound | Trichophython mentagrophytes | Aspergillus fumigatus | Candida albicans | Torulopsis glabrata |
|---|---|---|---|---|
| 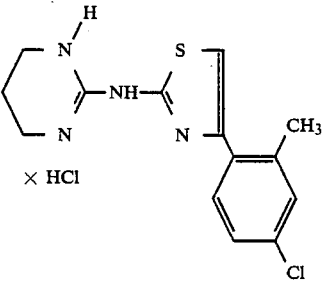 (C) (known) | >64 | >64 | >64 | >64 |
| 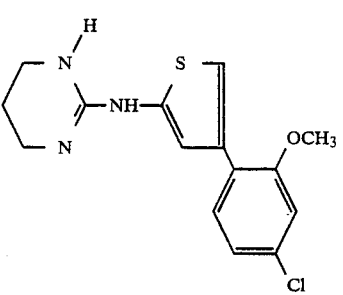 (3) | 0,25 | 4 | 32 | 64 |
| 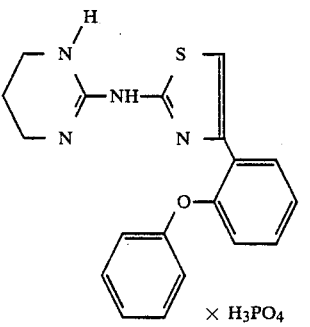 (6) | 0,25 | 4 | 32 | 64 |
| 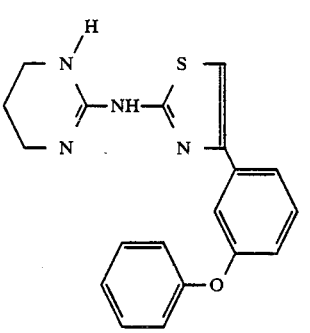 (16) | 0,25 | 4 | 32 | 64 |

TABLE A-continued
Antimycotic in vitro activity
MFC* values in μg/ml of nutrient medium
| Active compound | Trichophython mentagrophytes | Aspergillus fumigatus | Candida albicans | Torulopsis glabrata |
|---|---|---|---|---|
| 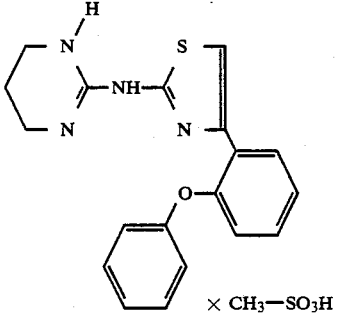 | | | | |
| (25) | 0,5 | 4 | 8 | 8 |
| 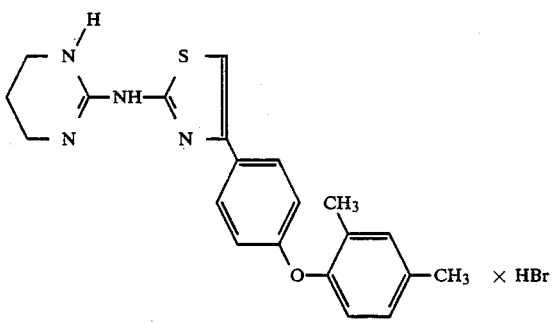 | | | | |
| (30) | 0,5 | 4 | 8 | 8 |
| 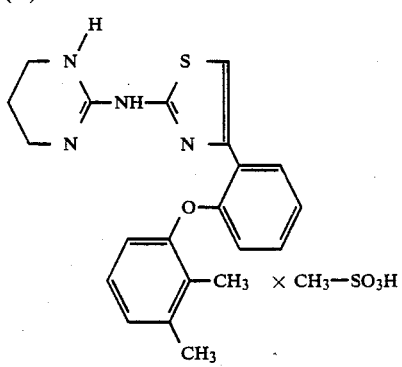 | | | | |
| (35) | 0,5 | 8 | 8 | 8 |
| 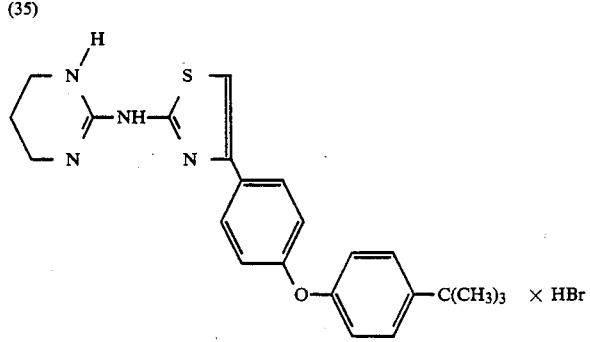 | | | | |
| (42) | 4 | 8 | 8 | 8 |

TABLE A-continued

Antimycotic in vitro activity
MFC* values in μg/ml of nutrient medium

| Active compound | Trichophython mentagrophytes | Aspergillus fumigatus | Candida albicans | Torulopsis glabrata |
|---|---|---|---|---|
| (45) [structure with Cl, CH₃ × HBr] | 0,25 | 4 | 8 | 8 |
| (47) [structure with Cl, CH₃ × HBr] | 0,25 | 4 | 8 | 8 |
| (48) [structure with Cl, CH₃ × CH₃—SO₃H] | ≦1 | 4 | 8 | 8 |
| (50) [structure with CH₃, Cl × HBr] | ≦1 | 4 | 8 | 8 |

TABLE A-continued

Antimycotic in vitro activity
MFC* values in µg/ml of nutrient medium

| Active compound | Trichophython mentagrophytes | Aspergillus fumigatus | Candida albicans | Torulopsis glabrata |
|---|---|---|---|---|
| (92) [structure with Cl, CH₃, O-phenyl, thiazoline-guanidine × CH₃—SO₃H] | 0,5 | 4 | 8 | 8 |
| (98) [structure with C₂H₅, O-phenyl, thiazoline-guanidine × CH₃—SO₃H] | ≦1 | 4 | 8 | 8 |
| (116) [structure with naphthyloxy-phenyl, thiazoline-guanidine × CH₃—SO₃H] | 0,5 | 4 | 8 | 8 |
| (132) [structure with SCF₃, CH₃, O-phenyl, thiazoline-guanidine × CH₃SO₃H] | 0,5 | 4 | 8 | 8 |

TABLE A-continued
Antimycotic in vitro activity
MFC* values in μg/ml of nutrient medium
| Active compound | Trichophython mentagrophytes | Aspergillus fumigatus | Candida albicans | Torulopsis glabrata |
|---|---|---|---|---|
| 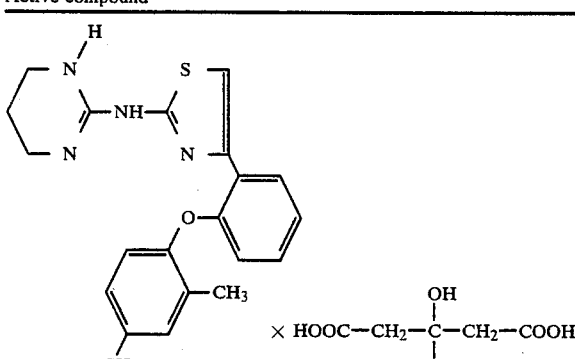 (133) | 0,5 | 4 | 8 | 8 |
| 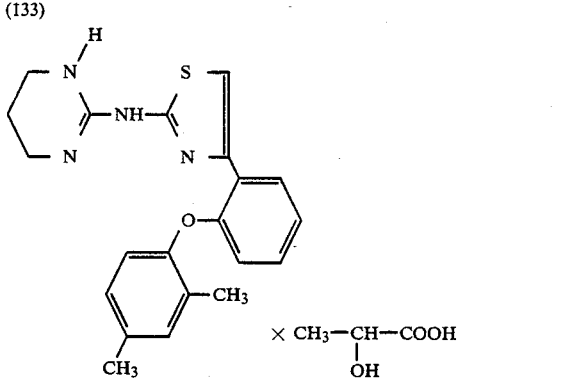 (134) | 0,5 | 4 | 8 | 8 |
| 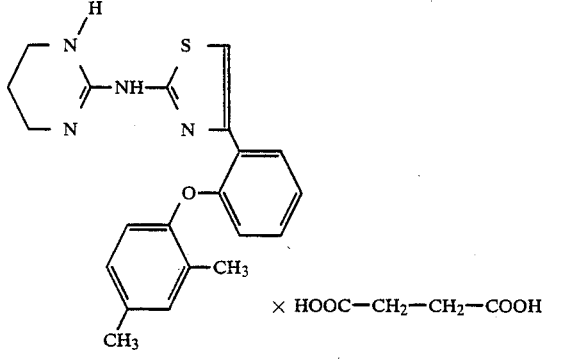 (135) | 0,5 | 4 | 8 | 8 |
| 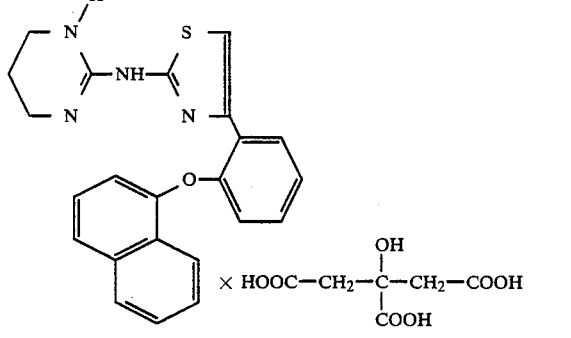 (137) | 0,5 | 4 | 8 | 8 |

TABLE A-continued

Antimycotic in vitro activity
MFC* values in μg/ml of nutrient medium

| Active compound | Trichophython mentagrophytes | Aspergillus fumigatus | Candida albicans | Torulopsis glabrata |
|---|---|---|---|---|
| (147) | 0,5 | 4 | 8 | 8 |
| (149) | 0,5 | 4 | 8 | 8 |
| (150) | 0,5 | 4 | 8 | 8 |
| (151) | 0,5 | 4 | 4 | 8 |

TABLE A-continued

Antimycotic in vitro activity
MFC* values in μg/ml of nutrient medium

| Active compound | Trichophython mentagrophytes | Aspergillus fumigatus | Candida albicans | Torulopsis glabrata |
|---|---|---|---|---|
| (153) | 0,5 | 4 | 4 | 8 |
| (181) | 0,5 | 8 | 4 | 4 |

*minimum fungicidal concentration of >99%

What is claimed is:
1. A 2-aminothiazole of the formula

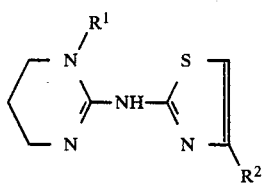

in which
R[1] represents hydrogen or straight-chain or branched alkyl having 1 to 4 carbon atoms and
R[2] represents a radical of the formula

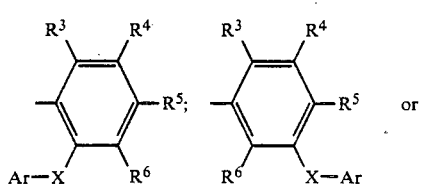

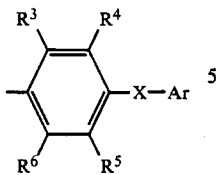

where
R³, R⁴, R⁵ and R⁶ independently of one another in each case represent hydrogen, fluorine, chlorine, bromine, iodine, nitro, in each case straight-chain or branched alkyl, alkoxy, alkoxycarbonyl, dialkylamino, alkylthio, alkylsulphinyl or alkylsulphonyl each having 1 to 4 carbon atoms in the respective alkyl moieties, or in each case straight-chain or branched halogenoalkyl, halogenoalkoxy, halogenalkylthio, halogenoalkylsulphiyl or halogenoalkylsulphonyl each having 1 to 4 carbon atoms and 1 to 9 identical or different halogen atoms.

X represents oxygen, sulphur, sulphinyl or sulphonyl and

Ar represents phenyl, α-naphthyl, β-naphthyl, tetrahydronaphthyl or indanyl which are in each case unsubstituted or substituted by identical or different substituents, suitable substituents in each case being: fluorine, chlorine, bromine, iodine, in each case straight-chain or branched alkyl, alkoxy, alkoxy-carbonyl, dialkylamino, alkylthio, alkylsulphinyl or alkylsulphonyl each having 1 to 8 carbon atoms in the respective alkyl moieties, in each case straight-chain or branched halogenoalkyl, halogenoalkoxy, halogenoalkylthio, halogenoalkylsulphinyl or halogenoalkylsulphonyl each having 1 to 4 carbon atoms and 1 to 9 identical or different halogen atoms, cycloalkyl having 3 to 7 carbon atoms, phenylalkyl or phenoxyalkyl each having 1 to 4 carbon atoms in the straight-chain or branched alkyl moiety and also phenyl or phenoxy.

2. A 2-aminothiazole according to claim 1, in which
R¹ represents hydrogen, methyl or ethyl,
R² represents a radical of the formula

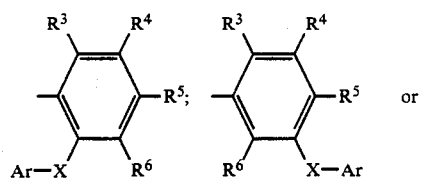

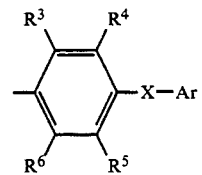

where
R³, R⁴, R⁵ and R⁶ independently of one another in each case represent hydrogen, fluorine, chlorine, bromine, nitro, methyl, ethyl, methoxy, ethoxy, methoxycarbonyl, ethoxycarbonyl, dimethylamino, diethylamino, methylthio, ethylthio, methylsulphinyl, ethylsulphinyl, methylsulphonyl, or ethylsulphonyl, or halogenomethyl, halogenoethyl, halogenmethoxy, halogenoethoxy, halogenomethylthio, halogenoethylthio, halogenomethylsulphinyl, halogenoethylsulphinyl, halogenomethylsulphonyl or halogenoethylsulphonyl each having 1 to 5 identical or different halogen atoms, X represents oxygen, sulphur, sulphinyl or sulphonyl and Ar represents phenyl, α-naphthyl, β-naphthyl, tetrahydronaphthyl or indanyl which are in each case unsubstituted or substituted by identical or different substituents, suitable substituents in each case being: fluorine, chlorine, bromine, nitro, in each case straight-chain or branched alkyl, alkoxy, alkoxycarbonyl or dialkylamino each having 1 to 6 carbon atoms in the respective alkyl moieties, in each case straight-chain or branched alkylthio, alkylsulphinyl or alkylsulphonyl each having 1 to 3 carbon atoms, in each case straight-chain or branched halogenoalkyl, halogenoalkoxy, halogenoalkylthio, halogenoalkylsulphinyl or halogenoalkylsulphonyl each having 1 to 3 carbon atoms and 1 to 7 identical or different halogen atoms, cyclohexyl having 3 to 6 carbon atoms, phenylalkyl or phenoxyalkyl each having 1 to 3 carbon atoms in the straight-chain or branched alkyl moiety and also phenyl or phenoxy.

3. A pharmaceutical composition useful for combating mycoses comprising an effective amount of a 2-aminothiazole according to claim 1 and a pharmaceutically acceptable excipient.

4. A method of combating mycoses comprising administering to a patient in need of such treatment an effective amount of a 2-aminothiazole according to claim 1.

5. A method of combating mycoses in warm blooded animals comprising administering to said animal an antimycotically effective amount of a 2-aminothiazole according to claim 1 either alone or in admixture with an inert excipient or in the form of a medicament.

6. A medicament in dosage unit form comprising an antimycotically effective amount of a 2-aminothiazole according to claim 1 either alone or in admixture with a suitable pharmaceutical excipient.

* * * * *

UNITED STATES PATENT AND TRADEMARK OFFICE
CERTIFICATE OF CORRECTION

PATENT NO. : 4,956,370

DATED : September 11, 1990

INVENTOR(S) : Ippen et al.

It is certified that error appears in the above-identified patent and that said Letters Patent is hereby corrected as shown below:

Col. 145, line 21    Delete " halogenalkylthio " and substitute -- halogenoalkylthio --

Col. 145, lines 21-22    Delete " halogenoalkylsulphiyl " and substitute -- halogenoalkylsulphinyl --

Col. 145, line 25    After " atoms " delete " . " and substitute -- , --

Col. 146, line 18    Delete " halogenmethoxy " and substitute -- halogenomethoxy --

Signed and Sealed this

Twenty-fifth Day of August, 1992

Attest:

DOUGLAS B. COMER

Attesting Officer    Acting Commissioner of Patents and Trademarks